United States Patent
Kelvin et al.

(10) Patent No.: US 7,332,294 B2
(45) Date of Patent: Feb. 19, 2008

(54) CXCL10-BASED DIAGNOSIS AND TREATMENT OF RESPIRATORY ILLNESSES

(75) Inventors: David Kelvin, London (CA); Mark J. Cameron, Mississauga (CA); Desmond Persad, Toronto (CA)

(73) Assignee: University Health Network, Toronto, Ontario (CA)

( * ) Notice: Subject to any disclaimer, the term of this patent is extended or adjusted under 35 U.S.C. 154(b) by 305 days.

(21) Appl. No.: 10/920,055

(22) Filed: Aug. 17, 2004

(65) Prior Publication Data

US 2006/0040329 A1 Feb. 23, 2006

(51) Int. Cl.
*G01N 33/53* (2006.01)
(52) U.S. Cl. .................................. 435/7.2; 424/1.41
(58) Field of Classification Search ............... None
See application file for complete search history.

(56) References Cited

OTHER PUBLICATIONS

Cook et al., Simultaneous measurement of six cytokines in a single sample of human tears using microparticle-based flow cytometry; allergics vs. non-allergics. J. Immunol. Method., 254, 109-118, 2001.*
Nicholls et al. Lung pathology of fatal severe acute respiratory syndrome. The Lancet, 361, 1773-1778, published on line May 16, 2003.*
Booth, C. M. et al. 2003. Clinical features and short-term outcomes of 144 patients with SARS in the greater Toronto area. JAMA 289:2801.
Centers for Disease Control and Prevention. 2003. Update: severe acute respiratory syndrome—worldwide and United States, 2003. MMWR Morb. Mortal. Wkly. Rep. 52:664.
Christen, U. et al. 2003. Among CRCR3 chemokines, IFN—inducible protein of 10 kDa (CXCchemokine ligand (CXCL) 10) but not monokine induced by IFN- (CXCL9) imprints a pattern for the subsequent development of autoimmune disease. J. Immunol. 171:683.
Cyranoski, D. 2004.. Swift response greets return of SARS in China. Nature 427:89.
Drosten, C. et al. 2003. Identification of a novel coronavirus in patients with severe acute respiratory syndrome. N. Engl. J. Med. 348:1967.
Dufour, J.H. et al. 2002. IFN—inducible protein 10 (IP-10; CXCL10)-deficient mice reveal a role for IP-10 in effector T cell generation and trafficking. J. Immunol. 168:3195.
Enserink, M. 2003. SARS researchers report new animal models. Science 302:213.
Hwang, D.M. et al. 2004. Pulmonary pathology of severe acute respiratory syndrome in Toronto. Mod. Pathol. online publication, Jul. 23, 2004; doi:10.1038/modpathol.3800247.
Knowles, S.R. et al. 2003. Common adverse events associated with the use of ribavirin for severe acute respiratory syndrome in Canada. Clin. Infect. Dis. 37:1139.
Ksiazek, T. G. et al. 2003. A novel coronavirus associated with severe acute respiratory syndrome, N. Engl. J. Med. 348:1953.
Kuiken, T. et al. 2003. Newly discovered coronavirus as the primary cause of severe acute respiratory syndrome. Lancet 362:263.
Lee, C.H. et al. 2004. Altered p38 mitogen-activated protein kinase expression in different leukocytes with increment of immunosuppressive mediators in patients with severe acute respiratory syndrome. J. Immunol. 172:7841.
Lee, N. et al, 2003. A major outbreak of severe acute respiratory syndrome in Hong Kong. N. Engl. J. Med. 348:1986.
Liu, M. T. et al. 2001. The CXC chemokines IP-10 and Mig are essential in host defense following infection with a neurotropic coronavirus. Adv. Exp. Med. Biol. 494:323.
Liu, M.T. et al. 2001. Neutralization of the chemokine CXCL10 reduces inflammatory cell invasion and demyelination and improves neurological function in a viral model of multiple sclerosis. J. Immunol. 167:4091.
Luster, A.D. 1998. Chemokines—Chemotactic cytokines that mediate inflammation. N. Engl. J. Med. 338:436.
Mazzulli, T. et al. 2004. Severe acute respiratory syndrome-associated Coronavirus in lung tissue. Emerg. Infect. Dis. 10:20.
Melchjorsen, J. et al. 2003, Expression and function of chemokines during viral infections: from molecular mechanisms to in vivo function. J. Leukoc. Biol. 74:331.
Ng, P. C. et al. 2004. Inflammatory cytokine profile in children with severe acute respiratory syndrome. Pediatrics 113:e7.
Nicholls, J. M. et al. 2003. Lung pathology of fatal severe acute respiratory syndrome. Lancet 361:1773.
Nicoletti, F. et al. 2002. Serum concentrations of the interferon-gamma-inducible chemokine IP-10/CXCL10 are augmented in both newly diagnosed Type I diabetes mellitus patients and subjects at risk of developing the disease. Diabetologia 45:1107.
Patel, D. D. et al. 2001. CXCR3 and CCR5 ligands in rheumatoid arthritis synovium. Clin. Immunol. 98:39.
Peiris, J. S. et al. 2003. Coronavirus as a possible cause of severe acute respiratory syndrome. Lancet 361:1319.
Poutanen, S. et al. 2003. Identification of severe acute respiratory syndrome in Canada. N. Engl. J. Med. 348:1995.
Ranieri, V. M. et al. 1999. Effect of mechanical ventilation on inflammatory mediators in patients with acute respiratory distress syndrome: a randomized controlled trial. JAMA 282:54.
Rossi, D., and Zlotnik, A. 2000. The biology of chemokines and their receptors. Annu. Rev. Immunol. 18:217.
Sauty, A., M. et al. 1999. The T cell-specific CXC chemokines IP-10, Mig, and I-TAC are expressed by activated human bronchial epithelial cells. J. Immunol. 162:3549.
Sorensen, T. L. et al. 2002. Multiple sclerosis: a study of CXCL10 and CXCR3 co-localization in the inflamed central nervous system. J. Neuroimmunol. 127:59.

(Continued)

*Primary Examiner*—Lorraine Spector
*Assistant Examiner*—Elly-Gerald Stoica
(74) *Attorney, Agent, or Firm*—Klarquist Sparkman LLP

(57) ABSTRACT

Elevated blood levels of the chemokine CXCL10 polypeptide are associated with respiratory illnesses (e.g. SARS, influenza and community-acquired pneumonia) and are useful in diagnosis of patients. Methods are provided for diagnosis and treatment of patients suffering from respiratory illnesses. Methods are provided for identifying inhibitors of the CXCL10:CXCR3 axis, for use in treating patients suffering from respiratory illnesses.

3 Claims, 9 Drawing Sheets

OTHER PUBLICATIONS

Sorensen, T.L. et al. 2001. Chemokines CXCL10 and CCL2: differential involvement in intrathecal inflammation in multiple sclerosis. Eur. J. Neurol. 8:665.

Trifilo, M.J. et al. 2004. CXC chemokine ligand 10 controls viral infection in the central nervous system: evidence for a role in innate immune response through recruitment and activation of natural killer cells. J. Virol. 78:585.

Tsang, K. W. et al. 2003. A cluster of cases of severe acute respiratory syndrome in Hong Kong. N. Engl. J. Med. 348:1977.

Wong, C.K. et al. 2004. Plasma inflammatory cytokines and chemokines in severe acute respiratory syndrome. Clin. Exp. Immunol. 136:95.

Younes, S. A. et al. 2003. HIV-1 viremia prevents the establishment of interleuken 2-producing HIV-specific memory CD4+ T cells endowed with proliferative capacity. J. Exp. Med. 198:1909.

Zheng, B. J. et al. 2004. SARS-related virus predating SARS outbreak, Hong Kong. Emerg. Infect. Dis. 10:176.

\* cited by examiner

SEQUENCE LISTING

<160> NUMBER OF SEQ ID NOS: 8

<210> SEQ ID NO 1
<211> LENGTH: 98
<212> TYPE: PRT
<213> ORGANISM: Homo sapiens

<400> SEQUENCE: 1

```
Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
            35                  40                  45

Glu Ile Ile Pro Ala Ser Gln Phe Cys Pro Arg Val Glu Ile Ile Ala
            50                  55                  60

Thr Met Lys Lys Lys Gly Glu Lys Arg Cys Leu Asn Pro Glu Ser Lys
65              70                  75                  80

Ala Ile Lys Asn Leu Leu Lys Ala Val Ser Lys Glu Met Ser Lys Arg
                85                  90                  95

Ser Pro

<210> SEQ ID NO 2
<211> LENGTH: 1172
<212> TYPE: DNA
<213> ORGANISM: Homo sapiens

<400> SEQUENCE: 2
gagacattcc tcaattgctt agacatattc tgagcctaca gcagaggaac ctccagtctc      60
agcaccatga tcaaactgc gattctgatt tgctgcctta tctttctgac tctaagtggc     120
attcaaggag tacctctctc tagaaccgta cgctgtacct gcatcagcat tagtaatcaa    180
cctgttaatc caaggtcttt agaaaaactt gaaattattc ctgcaagcca attttgtcca    240
cgtgttgaga tcattgctac aatgaaaaag aagggtgaga agagatgtct gaatccagaa    300
tcgaaggcca tcaagaattt actgaaagca gttagcaagg aaatgtctaa agatctcct    360 taaaaccaga ggggagcaaa atcgatgcag tgcttccaag gatggaccac acagaggctg    420
cctctcccat cacttcccta catggagtat atgtcaagcc ataattgttc ttagtttgca    480
gttacactaa aaggtgacca atgatggtca ccaaatcagc tgctactact cctgtaggaa    540
ggttaatgtt catcatccta agctattcag taataactct accctggcac tataatgtaa    600
gctctactga ggtgctatgt tcttagtgga tgttctgacc ctgcttcaaa tatttccctc    660 accttttccca tcttccaagg gtactaagga atctttctgc tttggggttt atcagaattc    720
tcagaatctc aaataactaa aaggtatgca atcaaatctg cttttttaaag aatgctcttt    780 acttcatgga cttccactgc catcctccca agggggccaa attctttcag tggctaccta    840
catacaattc caaacacata caggaaggta gaaatatctg aaaatgtatg tgtaagtatt    900
cttatttaat gaaagactgt acaaagtata agtcttagat gtatatattt cctatattgt    960
tttcagtgta catggaataa catgtaatta agtactatg atcaatgagt aacaggaaaa   1020
ttttaaaaat acagatagat atatgctctg catgttacat aagataaatg tgctgaatgg   1080
ttttcaaata aaaatgaggt actctcctgg aaatattaag aaagactatc taatgttga    1140 aagatcaaaa ggttaataaa gtaattataa ct                                 1172

<210> SEQ ID NO 3
<211> LENGTH: 98
<212> TYPE: PRT
<213> ORGANISM: Murinae gen. sp.

<400> SEQUENCE: 3

Met Asn Pro Ser Ala Ala Val Ile Phe Cys Leu Ile Leu Leu Gly Leu
1               5                   10                  15
```

-continued

```
Ser Gly Thr Gln Gly Ile Pro Leu Ala Arg Thr Val Arg Cys Asn Cys
         20                  25                  30

Ile His Ile Asp Asp Gly Pro Val Arg Met Arg Ala Ile Gly Lys Leu
             35                  40                  45

Glu Ile Ile Pro Ala Ser Leu Ser Cys Pro Arg Val Glu Ile Ile Ala
     50                  55                  60

Thr Met Lys Lys Asn Asp Glu Gln Arg Cys Leu Asn Pro Glu Ser Lys
 65                  70                  75                  80

Thr Ile Lys Asn Leu Met Lys Ala Phe Ser Gln Lys Arg Ser Lys Arg
                 85                  90                  95

Ala Pro

<210> SEQ ID NO 4
<211> LENGTH: 1063
<212> TYPE: DNA
<213> ORGANISM: Murinae gen. sp.

<400> SEQUENCE: 4
catcccgagc caaccttccg gaagcctccc catcagcacc atgaacccaa gtgctgccgt      60
cattttctgc ctcatcctgc tgggtctgag tgggactcaa gggatccctc tcgcaaggac     120
ggtccgctgc aactgcatcc atatcgatga cgggccagtg agaatgaggg ccatagggaa     180
gcttgaaatc atccctgcga gcctatcctg cccacgtgtt gagatcattg ccacgatgaa     240
aaagaatgat gagcagagat gtctgaatcc ggaatctaag accatcaaga atttaatgaa     300
agcgtttagc caaaaaaggt ctaaaagggc tccttaactg gagtgaagcc acgcacacac     360
cccggtgctg cgatggatgg acagcagaga gcctctctcc atcactcccc tttacccagt     420
ggatggctag tcctaattgc ccttggtctt ctgaaaggtg accagccgtg gtcacatcag     480
ctgctactcc tcctgcagga tgatggtcaa gccatggtcc tgagacaaaa gtaactgccg     540
aagcaagaat tctttaaggg ctggtctgag tcctcgctca gtggctggga tggctgtcc     600 tagctctgta ctgtaagcta tgtggaggtg cgacgccctt caccatgtgc catgcccagg     660
ctgctcccca cacctccttt gtcctcccta gctcaggctc gtcagttcta agtttacctg     720
agctctttta tttcagatgt aagactacaa atttaagttt gtaagcacga acttaaccac     780
catcttccca aggggttatc aagatactca gaggaacctg aaaatgtatg tgtaaatact     840
atttaatgaa cgactgtaca aagtagaatt cctaatgtat ttttttgtatg ctttgcattg     900 tatatggaag aacttgtgtc atcaagtatg tatcaatggg tagttaaagt ttattttaa      960 aaccgtccaa taccttttgt attatgtaac attcaaaaga caatgtactg tattgaaagt    1020
agtaagagac ccaaaatgta ataaagtaat aataactgac atg                      1063

<210> SEQ ID NO 5
<211> LENGTH: 1670
<212> TYPE: DNA
<213> ORGANISM: Homo sapiens

<400> SEQUENCE: 5
ccaaccacaa gcaccaaagc agaggggcag gcagcacacc cccagcagc cagagcacca      60 gcccagccat ggtccttgag gtgagtgacc accaagtgct aaatgacgcc gaggttgccg     120
ccctcctgga gaacttcagc tcttcctatg actatggaga aaacgagagt gactcgtgct     180
gtacctcccc gcctgcccca caggacttca gcctgaactt cgaccgggcc ttcctgccag     240 cccctctacag cctcctcttt ctgctggggc tgctgggcaa cggcgcggtg gcagccgtgc     300
```

```
tgctgagccg gcggacagcc ctgagcagca ccgacacctt cctgctccac ctagctgtag    360
cagacacgct gctggtgctg acactgccgc tctgggcagt ggacgctgcc gtccagtggg    420
tctttggctc tggcctctgc aaagtggcag gtgccctctt caacatcaac ttctacgcag    480
gagccctcct gctggcctgc atcagctttg accgctacct gaacatagtt catgccaccc    540
agctctaccg ccgggggccc ccggcccgcg tgaccctcac ctgcctggct gtctggggc     600
tctgcctgct tttcgccctc ccagacttca tcttcctgtc ggccaccac gacgagcgcc     660
tcaacgccac ccactgccaa tacaacttcc cacaggtggg ccgcacggct ctgcgggtgc    720
tgcagctggt ggctggcttt ctgctgcccc tgctggtcat ggcctactgc tatgcccaca    780
tcctggccgt gctgctggtt ccagggggcc agcggcgcct gcgggccatg cggctggtgg    840
tggtggtcgt ggtggccttt gccctctgct ggaccccta tcacctggtg gtgctggtgg    900
acatcctcat ggacctgggc gctttggccc gcaactgtgg ccgagaaagc agggtagacg    960
tggccaagtc ggtcacctca ggcctgggct acatgcactg ctgcctcaac ccgctgctct   1020
atgcctttgt aggggtcaag ttccgggagc ggatgtggat gctgctcttg cgcctgggct   1080
gccccaacca gagagggctc cagaggcagc atcgtcttc ccgccgggat tcatcctggt   1140
ctgagacctc agaggcctcc tactcgggct tgtgaggccg gaatccgggc tccccttcg    1200
cccacagtct gacttccccg cattccaggc tcctccctcc ctctgccggc tctggctctc   1260
cccaatatcc tcgctcccgg gactcactgg cagccccagc accaccaggt ctcccgggaa   1320
gccaccctcc cagctctgag gactgcacca ttgctgctcc ttagctgcca agccccatcc   1380
tgccgcccga ggtggctgcc tggagcccca ctgcccttct catttggaaa ctaaaacttc   1440
atcttcccca agtgcgggga gtacaaggca tggcgtagag ggtgctgccc catgaagcca   1500
cagcccaggc ctccagctca gcagtgactg tggccatggt ccccaagacc tctatatttg   1560
ctctttttatt tttatgtcta aaatcctgct taaaactttt caataaacaa gatcgtcagg   1620
accaaaaaaa aaaaaaaaaa aaaaaaaaaa aaaaaaaaaa aaaaaaaaaa                1670
```

<210> SEQ ID NO 6
<211> LENGTH: 368
<212> TYPE: PRT
<213> ORGANISM: Homo sapiens

<400> SEQUENCE: 6

```
Met Val Leu Glu Val Ser Asp His Gln Val Leu Asn Asp Ala Glu Val
1               5                   10                  15

Ala Ala Leu Leu Glu Asn Phe Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
```

-continued

```
            130                 135                 140
Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
                180                 185                 190

His His Asp Glu Arg Leu Asn Ala Thr His Cys Gln Tyr Asn Phe Pro
                195                 200                 205

Gln Val Gly Arg Thr Ala Leu Arg Val Leu Gln Leu Val Ala Gly Phe
210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Ala Phe Ala Leu Cys Trp Thr Pro Tyr His
                260                 265                 270

Leu Val Val Leu Val Asp Ile Leu Met Asp Leu Gly Ala Leu Ala Arg
                275                 280                 285

Asn Cys Gly Arg Glu Ser Arg Val Asp Val Ala Lys Ser Val Thr Ser
290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Arg Leu
                325                 330                 335

Gly Cys Pro Asn Gln Arg Gly Leu Gln Arg Gln Pro Ser Ser Ser Arg
                340                 345                 350

Arg Asp Ser Ser Trp Ser Glu Thr Ser Glu Ala Ser Tyr Ser Gly Leu
                355                 360                 365

<210> SEQ ID NO 7
<211> LENGTH: 367
<212> TYPE: PRT
<213> ORGANISM: Murinae gen. sp.

<400> SEQUENCE: 7

Met Tyr Leu Glu Val Ser Glu Arg Gln Val Leu Asp Ala Ser Asp Phe
1               5                   10                  15

Ala Phe Leu Leu Glu Asn Ser Thr Ser Pro Tyr Asp Tyr Gly Glu Asn
                20                  25                  30

Glu Ser Asp Phe Ser Asp Ser Pro Pro Cys Pro Gln Asp Phe Ser Leu
            35                  40                  45

Asn Phe Asp Arg Thr Phe Leu Pro Ala Leu Tyr Ser Leu Leu Phe Leu
        50                  55                  60

Leu Gly Leu Leu Gly Asn Gly Ala Val Ala Ala Val Leu Leu Ser Gln
65                  70                  75                  80

Arg Thr Ala Leu Ser Ser Thr Asp Thr Phe Leu Leu His Leu Ala Val
                85                  90                  95

Ala Asp Val Leu Leu Val Leu Thr Leu Pro Leu Trp Ala Val Asp Ala
                100                 105                 110

Ala Val Gln Trp Val Phe Gly Pro Gly Leu Cys Lys Val Ala Gly Ala
            115                 120                 125

Leu Phe Asn Ile Asn Phe Tyr Ala Gly Ala Phe Leu Leu Ala Cys Ile
        130                 135                 140
```

```
Ser Phe Asp Arg Tyr Leu Ser Ile Val His Ala Thr Gln Ile Tyr Arg
145                 150                 155                 160

Arg Asp Pro Arg Val Arg Val Ala Leu Thr Cys Ile Val Val Trp Gly
                165                 170                 175

Leu Cys Leu Leu Phe Ala Leu Pro Asp Phe Ile Tyr Leu Ser Ala Asn
            180                 185                 190

Tyr Asp Gln Arg Leu Asn Ala Thr His Cys Gln Tyr Asn Phe Pro Gln
        195                 200                 205

Val Gly Arg Thr Ala Leu Arg Val Leu Gln Leu Val Ala Gly Phe Leu
    210                 215                 220

Leu Pro Leu Leu Val Met Ala Tyr Cys Tyr Ala His Ile Leu Ala Val
225                 230                 235                 240

Leu Leu Val Ser Arg Gly Gln Arg Arg Phe Arg Ala Met Arg Leu Val
                245                 250                 255

Val Val Val Val Ala Ala Phe Ala Val Cys Trp Thr Pro Tyr His Leu
            260                 265                 270

Val Val Leu Val Asp Ile Leu Met Asp Val Gly Val Leu Ala Arg Asn
        275                 280                 285

Cys Gly Arg Glu Ser His Val Asp Val Ala Lys Ser Val Thr Ser Gly
    290                 295                 300

Met Gly Tyr Met His Cys Cys Leu Asn Pro Leu Leu Tyr Ala Phe Val
305                 310                 315                 320

Gly Val Lys Phe Arg Glu Gln Met Trp Met Leu Phe Thr Arg Leu Gly
                325                 330                 335

Arg Ser Asp Gln Arg Gly Pro Gln Arg Gln Pro Ser Ser Arg Arg
            340                 345                 350

Glu Ser Ser Trp Ser Glu Thr Thr Glu Ala Ser Tyr Leu Gly Leu
        355                 360                 365

<210> SEQ ID NO 8
<211> LENGTH: 1608
<212> TYPE: DNA
<213> ORGANISM: Murinae gen. sp.

<400> SEQUENCE: 8
gcaagttccc aaccacaagt gccaaaggca gagaagcagg cagcacgaga cctgacccca      60
gcagccacag ccggagcacc agccaagcca tgtaccttga ggttagtgaa cgtcaagtgc     120
tagatgcctc ggactttgcc tttcttctgg aaaacagcac ctctccctac gattatgggg     180
aaaacgagag cgacttctct gactccccgc cctgcccaca ggatttcagc ctgaactttg     240
acagaacctt cctgccagcc ctctacagcc tcctcttctt gctggggctg ctaggcaatg     300
gggcggtggc tgctgtgcta ctgagtcagc gcactgccct gagcagcacg acaccttcc      360 tgctccacct ggctgtagcc gatgttctgc tggtgttaac tcttccattg tgggcagtgg     420
atgctgctgt ccagtgggtt ttcggccctg gcctctgcaa agtggcaggc gccttgttca     480
acatcaactt ctatgcaggg gccttcctgc tggcttgtat aagcttcgac agatatctga     540
gcatagtgca cgccacccag atctaccgca gggaccccg ggtacgtgta gccctcacct      600
gcatagttgt atggggtctc tgtctgctct ttgccctccc agatttcatc tacctatcag     660
ccaactacga tcagcgcctc aatgccaccc attgccagta caacttccca caggtgggtc     720
gcactgctct gcgtgtactg cagctagtgg ctggtttcct gctgcccctt ctggtcatgg     780
cctactgcta tgcccatatc ctagctgttc tgctggtctc cagaggccag aggcgttttc     840
gagctatgag gctagtggta gtggtggtgg cagcctttgc tgtctgctgg acccctatc      900
```

-continued

```
acctggtggt gctagtggat atcctcatgg atgtgggagt tttggcccgc aactgtggtc    960
gagaaagcca cgtggatgtg gccaagtcag tcacctcggg catggggtac atgcactgct   1020
gcctcaatcc gctgctctat gcctttgtgg gagtgaagtt cagagagcaa atgtggatgt   1080
tgttcacgcg cctgggccgc tctgaccaga gagggcccca gcggcagccg tcatcttcac   1140
ggagagaatc atcctggtct gagacaactg aggcctccta cctgggcttg taattctgga   1200
ctggaactgt agcctgcgca gcccaagtcc taacacactc caagtgcttg tcctcctggt   1260
agttgggcta gctcgaactt acccgtaact ttgctgccag gatgcactga cagctcagca   1320
tatatccagc tctcctgaga atcaatctca gcaacaagga caacaccatt actgtgcctt   1380
agctgccatg ccctatcttg ctgttttaga actagctgcc tggagcccca ccgccctact   1440
aaattagcaa gtagaactca gccatccctg tgtgagaaga gggagaggca aatagcacag   1500
agggccaggc gttgtcagca ctgaatgtgc ccatctcagt atctcaatat ttgcccaatt   1560
ttatttctag aaacctcact taaactttca ataaacaagg taatgagg               1608
```

CXCL10-BASED DIAGNOSIS AND TREATMENT OF RESPIRATORY ILLNESSES

FIELD OF THE INVENTION

The invention relates to the diagnosis and treatment of patients suffering from respiratory illnesses, e.g. Severe Acute Respiratory Syndrome (SARS), influenza, and community-acquired pneumonia. Elevated blood levels of CXCL10 polypeptide are associated with respiratory illnesses and are useful in diagnosis and prognosis of patients. Methods are provided for treating respiratory illnesses by inhibiting the CXCL10:CXCR3 axis. Methods are also provided for identifying inhibitors of the CXCL10:CXCR3 axis, for use in treating patients suffering from respiratory illnesses.

BACKGROUND OF THE INVENTION

Respiratory illnesses (e.g. community-acquired pneumonia, influenza and SARS) are a major public health concern.

Severe acute respiratory syndrome (SARS) emerged in late 2002 from its purported origins in Guangdong Province, China and infected over 8400 persons worldwide to date with an accompanying case fatality rate of approximately 11% (1-4, World Health Organization, http://www.who.int/csr/sars/country/en/country2003_08_15.pdf).

A novel coronavirus (CoV), causing a spectrum of disease ranging from non-specific flu-like symptoms and lung inflammation to acute respiratory distress syndrome (ARDS) requiring intensive care, has been identified as the etiologic agent of SARS (5-8). While the SARS CoV epidemic of 2003 was largely contained through public health measures, it is unknown whether or not human SARS CoV will cause another global outbreak. With the confirmation of new unrelated SARS cases in China (9) and the finding that SARS CoV-related viruses infected persons in Hong Kong at least 2 years prior to the 2003 outbreak (10), it is clear that SARS will not easily be eradicated and that jumps from animals to humans will continue.

Lungs from patients with severe SARS show extensive acute injury with diffuse alveolar damage, acute vascular and endothelial injury and extensive immune infiltration (11-13). The molecular, cellular and pathological determinants that lead to lung injury and poor outcome in SARS are presently unclear; however the severity of SARS CoV infection may be partially determined by the immune system and dysregulated proinflammatory cytokines and chemokines (14-16).

SUMMARY OF THE INVENTION

In one aspect, the present invention provides a method for diagnosing respiratory illness in a patient, the method comprising detecting CXCL10 polypeptide in a biological sample from a patient, wherein an elevated level of CXCL10 polypeptide in said sample relative to a healthy control is diagnostic or prognostic of respiratory illness.

In another aspect, the present invention provides a commercial package comprising means for detecting CXCL10 polypeptide in a biological sample from a patient, together with instructions for use for diagnosis and/or prognosis of respiratory illness in a patient or for monitoring treatment thereof.

In another aspect, the present invention provides the use of CXCL10 polypeptide in the diagnosis of respiratory illness, wherein said CXCL10 polypeptide is contained in a biological sample from a patient and wherein an elevated level of CXCL10 polypeptide in said sample relative to a healthy control is diagnostic or prognostic of respiratory illness.

In another aspect, the present invention provides a method for treating a patient suffering from respiratory illness, the method comprising administering a compound that inhibits the CXCL10:CXCR3 axis.

In another aspect, the present invention provides a method for identifying a therapeutic agent for treating a respiratory illness, the method comprising:
(a) providing a test compound;
(b) providing a cell that expresses a polypeptide selected from CXCL10 polypeptide and CXCR3 polypeptide when cultured under suitable conditions in vitro; and
(c) detecting whether the test compound inhibits expression of said polypeptide by said cell.

In another aspect, the present invention provides a method for identifying a therapeutic agent for treating respiratory illness, the method comprising:
(a) providing a test compound;
(b) providing a polypeptide selected from CXCL10 polypeptide or CXCR3 polypeptide; and
(c) detecting whether the test compound binds to said polypeptide.

In another aspect, the present invention provides a method for identifying a therapeutic agent for treating respiratory illness, the method comprising:
(a) providing a test compound;
(b) providing a polypeptide selected from CXCL10 polypeptide or CXCR3 polypeptide;
(c) providing a binding partner that binds to said polypeptide; and
(d) detecting whether the test compound inhibits binding of said binding partner to said polypeptide.

In another aspect, the present invention provides a therapeutic agent for treating respiratory illness identified by the screening method of the invention.

In another aspect, the present invention provides a pharmaceutical composition for treating respiratory illness comprising the therapeutic agent a therapeutic agent identified by the screening method of the invention.

DETAILED DESCRIPTION OF THE INVENTION

Figure 1A:
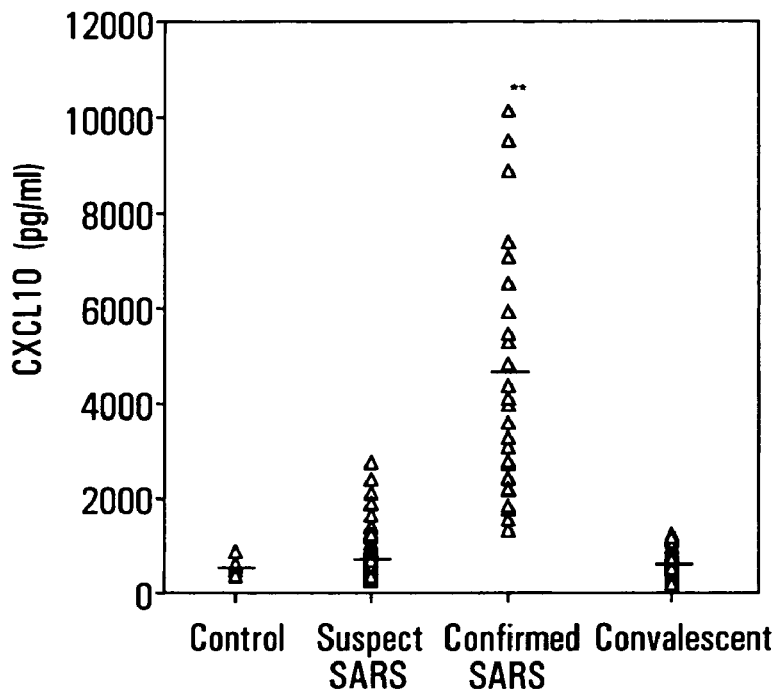
FIG. 1. High plasma concentrations of CXCL10 polypeptide in SARS patients. CXCL10 polypeptide (FIG. 1A) and CXCL9 (FIG. 1D) were measured in plasma from suspect (n=80) and confirmed (n=34) SARS patients within 48 hours of onset of symptoms by CBA. CXCL10 polypeptide and CXCL9 levels were also recorded healthy controls (n=14) and convalescents (n=63). Higher levels of CXCL10 polypeptide were measured in SARS patients relative to the other 3 groups (** P<0.0001). Other group comparisons revealed no further statistically significant differences. CXCL10 polypeptide (FIG. 1B, 1C) and CXCL9 (FIG. 1E, 1F) were measured in 25 confirmed SARS patients (FIG. 1B, 1E) and 10 confirmed SARS patients in the intensive care unit (ICU) (FIG. 1C, 1F). * significantly lower points of CXCL10 polypeptide expression at 16-40 days in confirmed SARS patients compared to those in the ICU (* P<0.05). Solid lines represent consecutive measurements in the same patient and † indicates deceased. Curves produced by nonlinear regression analysis (hatched lines).
Figure 1B:
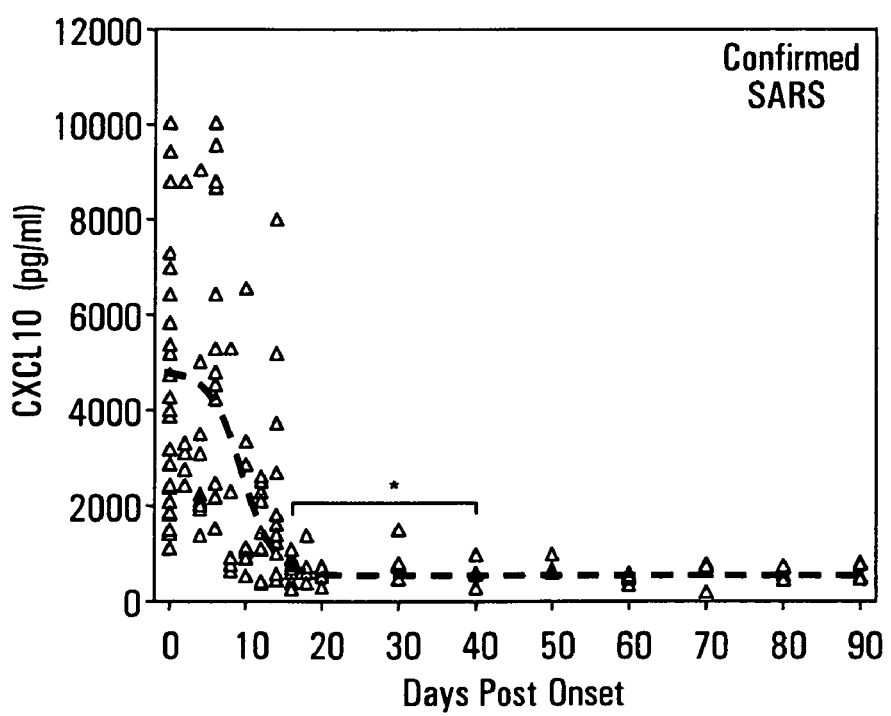

Previous findings indicate that CXCL10 polypeptide (IFN-γ inducible protein 10/IP-10) is associated with host defense in murine models of non-SARS coronavirus infections (17-20).

We profiled the CXCL10:CXCR3 axis in patients of different SARS diagnosis, status and outcome throughout their disease and utilized two non-human primate models of SARS CoV infection to confirm select findings. We found that the lung tropism of SARS CoV could be linked with early expression of CXCL10 polypeptide in the plasma and lungs of SARS patients, which in turn could regulate infiltration of SARS antigen-specific T cells and potentially result in an uncontrollable immune responses against SARS CoV. Our data suggest that lung injury in SARS patients may result from an unabated proinflammatory immune responses against the SARS CoV involving CXCL10 polypeptide and its receptor CXCR3 polypeptide.

Thus, our data shows that the CXCL10:CXCR3 axis plays a key role in SARS disease course and lung injury and represents an important therapeutic target.

We obtained specimens within 24-48 hours of onset of symptoms from both confirmed SARS patients and non-SARS patients with SARS-like symptoms (suspect SARS in FIG. 1). Our longitudinal study also delineated patients suffering from mild to moderate or severe forms of the disease in the intensive care unit (ICU). Wong et al. described CXCL10 polypeptide increases during the early phase of infection relative to healthy controls in a recent study of plasma levels of cytokines and chemokines in a Hong Kong cohort of SARS patients (15), however our study is the first to associate the CXCL10:CXCR3 axis with a unique role in the evolution of SARS illness.

CXCL10 polypeptide was significantly elevated in all SARS patients and only slightly elevated in a few suspect cases. In patients with a severe course of disease, plasma levels of CXCL10 polypeptide remained elevated for weeks whereas CXCL10 polypeptide levels decreased more quickly to normal levels in patients with mild disease. Steroids appeared to have little effect on CXCL10 polypeptide levels since expression of CXCL10 polypeptide persisted in both SARS patients with mild disease and those with severe disease after steroid therapy commenced (typically 3-5 d post-onset of symptoms), at least until the patient began to recover. Moreover, an ICU patient with the highest sustained levels of plasma CXCL10 polypeptide died of SARS while undergoing immunosuppressive therapy to prevent graft rejection and aggressive steroid therapy for SARS (FIG. 1). Indeed, it has been shown that elevated levels of CXCL10 polypeptide in multiple sclerosis patients are not affected by steroid treatment (23) and CXCL10 polypeptide expression in bronchial epithelial cells is not affected by steroid treatment (24). We do not yet know what causes the long-term increased levels of CXCL10 polypeptide in the plasma of critical care patients, however mechanical injury due to ventilation culminating in ARDS may be responsible for continued CXCL10 polypeptide induction (25). On the other hand, this may only represent a partial explanation since whether or not a patient had cleared the virus, not whether or not mechanical ventilation was required, was more strongly correlated with changes in plasma CXCL10 polypeptide levels. Indeed, it has been shown that lung tissues from deceased SARS patients remain infected with SARS CoV (12,13).

The SARS patients profiled in this study comprised a highly diverse cohort with many variables in its composition, such as demographics, symptom presentation, course of illness and treatment, clinical features and parameters, microbiology, comorbidities and adverse events. Non-human primate models for SARS have been developed where symptoms in macaques are consistent with mild forms of SARS in humans, such as lung inflammation, alveolar damage and pneumonia, following experimental inocculation with SARS CoV (26,27). Using two non-human primate models of SARS infection we confirmed that CXCL10 polypeptide expression is indeed upregulated in vivo in SARS-infected rhesus and cynomolgus macaques in the early stages of infection with SARS CoV (Tor2).

Antiviral cellular responses are dependent on the production of cytokines, especially type I and II interferons and chemokines. Chemokines are known for their roles in cell recruitment but they can also activate immune cells and shape Th1/Th2 responses (28,29). In fact, chemokine expression can be induced upon viral entry into a cell (30). Based on the fact that SARS CoV induces CXCL10 polypeptide expression directly in infected VERO E6 cells, we suggest that as SARS CoV establishes infection, CXCL10 polypeptide is induced during primary lung inflammation. CXCR3 polypeptide, the receptor for CXCL10 polypeptide, plays a potent role in regulating migration of activated T cells (especially Th1 cells) to sites of inflammation (28).

We expect that the tropism of coronaviruses in general induces localized expression of CXCL10 polypeptide and subsequent recruitment of CXCR3 polypeptide-bearing lymphocytes. In keeping with this idea, we found elevated RNA levels of CXCR3 polypeptide in the lungs of deceased SARS-infected individuals, increased RNA levels of CXCR3 polypeptide in PBMCs and expression of cell surface CXCR3 polypeptide on SARS CoV N antigen-specific T cells with high proliferative capacity.

Others have demonstrated a role for CXCL10 polypeptide in the immunopathology of CoV infections in murine models of other diseases (17-20). CXCL10 polypeptide seems to be important for clearance of CoV and may also regulate autoinflammatory events that lead to severe pathogenesis in these models, as well as human autoimmune inflammatory diseases (31-33).

Based on our findings, we propose that CXCL10 polypeptide plays a dual role in SARS CoV infections. Elevation of CXCL10 polypeptide in 100% of SARS-infected individuals early in their disease indicates that it is a necessary host response to clear SARS CoV through the recruitment of antigen-specific effector CXCR3 polypeptide-bearing T cells, however in a minority of patients CXCL10 polypeptide may participate in SARS pathogenesis through the continued recruitment of activated T cell and mononuclear infiltrates resulting in tissue destruction and eventual organ failure. Once again, lung tissues from deceased SARS patients express high levels of CXCL10 polypeptide (FIG. 2) and remain infected with SARS CoV (12,13).

Previous studies have shown that CXCL10 polypeptide can be induced by IFN-γ under certain conditions. We found statistically significant increases (3-5 fold) in IFN-γ levels in the plasma of SARS patients at onset relative to healthy controls and convalescents (data not shown) indicating that IFN-γ-induced expression of CXCL10 polypeptide may play a role in the SARS disease course.

We expect that certain other viral infections can drive expression of CXCL10 polypeptide early in the course of infection. Our preliminary data indicates that some cases of West Nile Virus infection and community-acquired pneumonia are associated with small short-term increases of CXCL10 polypeptide. We have found that those infections also drive the expression of CXCL9, a closely related non-ELR chemokine that also binds CXCR3 polypeptide (data not shown). This finding is in contrast to SARS, where levels of CXCL9 could not be associated with disease onset, course or severity. This disparate involvement of CXCL10 polypeptide versus CXCL9 has been noted in studies of autoimmune disease (34).

We have shown that an early pattern of high levels of circulating CXCL10 polypeptide in the absence of CXCL9 is associated with a SARS CoV infection. Our data supports a model in which lung tropism of SARS CoV induces early expression of CXCL10 polypeptide in the lungs that in turn regulates infiltration of SARS antigen-specific T cells, thereby mediating immune responses against SARS CoV. The relationship between elevated and sustained levels of CXCL10 polypeptide and poor outcome in SARS patients may be a result of CXCL10 polypeptide recruitment of autoinflammatory cells and the failure of the immune system to clear the SARS CoV. While CXCL10 polypeptide may play a role in the establishment of other respiratory diseases, including those induced virally, patients suffering from inflammatory lung disease may benefit from strategies that neutralize or inhibit the pivotal function of the CXCL10: CXCR3 axis.

Based on our findings in patients infected with SARS, we predicted that the CXCL10:CXCR3 axis may play a role in other respiratory infections (such as influenza, especially influenza A, and community-acquired pneumonia, which may be of viral, bacterial, or atypical (unknown) origin), i.e. that other infectious respiratory agents could drive the expression of CXCL10 polypeptide during the course of infection. Our data show that this is indeed the case. Community-acquired pneumonia refers to a set of potentially severe lung infections acquired outside of hospitals. Common pathogens responsible for community-acquired pneumonia infections are Streptococcus pneumoniae, Haemophilus influenzae, Mycoplasma pneumoniae, influenza A, Legionella, Moraxella catarrhalis, Mycobacterium tuberculosis, and Chlamydophilia pneumoniae. The causative agent of community acquired pneumonia can remain unidentified in up to 50% of cases (atypical pneumonia). Our data comparing chest X-Ray positive (immune infiltrated) SARS patients with chest X-Ray positive patients with the various forms of community acquired pneumonia indicated that CXCL10 polypeptide plays a role in the establishment of severe cases of these other respiratory diseases. Therefore patients suffering from multiple forms of serious inflammatory lung disease may benefit from the diagnostic and prognostic properties of the CXCL10:CXCR3 axis and well as therapies that neutralize or inhibit the pivotal function of the CXCL10:CXCR3 axis.

In the present context, patients suffering from "severe SARS" are those SARS patients requiring increased levels of supplemental oxygen (i.e. those with PaO2/FiO2 readings<200), supplied by mask or intubation, and/or admission to the intensive care unit.

The time course of SARS disease highly variable. Mild cases of SARS typically last 14-20 days. However, severe cases of SARS can require 2-3 months of hospitalization.

CXCL10 Polypeptides and CXCR3 Polypeptides and Polynucleotides Encoding Them

"CXCL10" belongs to the α-chemokine (C—X—C) family and is also referred to as "Interferon-γ inducible protein 10 kD" or "IP-10". Several CXCL10 polypeptide amino acid sequences and nucleotide sequences encoding them are known, including for example:
(1) Human CXCL10 polypeptide amino acid sequence: GenBank accession No. NP_001556.1.
(2) Human CXCL10 polypeptide mRNA sequence: GenBank accession No. NM_001565.
(3) Murine CXCL10 polypeptide amino acid sequence: GenBank accession No. NP_067249.1.
(4) Murine CXCL10 polypeptide mRNA sequence: GenBank accession No. NM_021274.1.

"CXCR3" amino acid sequences and nucleotide sequences encoding them are also known, including for example:
(1) Human CXCR3 polypeptide mRNA sequence: GenBank accession No. NM_001504.
(2) Human CXCR3 polypeptide amino acid sequence: GenBank accession No. NP_001495.
(3) Murine CXCR3 polypeptide amino acid sequence: GenBank accession No. NP_034040.1.
(4) Murine CXCR3 polypeptide mRNA sequence: GenBank accession No. NM_009910.1.

As defined herein, the expressions "CXCL10 polypeptide" and "CXCR3 polypeptide" include variants of native CXCL10 polypeptide and CXCR3 polypeptide, for example: deletions, including truncations and fragments; insertions and additions, including tagged polypeptides and fusion proteins; substitutions, for example site-directed mutants and allelic variants; modifications, including for example peptoids having one or more non-amino acyl groups (q.v., sugar, lipid, etc.) covalently linked to the peptide and post-translational modifications; and peptidomimetics.

As used herein, "polypeptide" means any chain of amino acids, regardless of length or post-translational modification (e.g., glycosylation or phosphorylation), and include: natural proteins; synthetic or recombinant polypeptides and peptides as well as hybrid molecules (e.g. a fusion protein or chimera having one portion comprising all or part of a polypeptide of the invention and a second portion comprising an amino acid sequence from another protein or peptide); modified peptides, including for example peptoids having one or more non-amino acyl groups (q.v., sugar, lipid, etc.) covalently linked to the peptide; and peptidomimetics. Typically the protein or polypeptide may be isolated or substantially pure or recombinant. In the present context, polypeptides can have a length of for example at least 6, 8, 10, 12, 14, 16, 18, 20, 50, 100, 200, 300, 400, 500, etc. amino acids.

The term "polynucleotide" refers to a polymeric form of nucleotides of any length (e.g. at least 9, 12, 15, 18, 20, 50, 100, 200, 500, 1000, 2000, etc. nucleotides) and may also be referred to in the art as a "nucleic acid" or "nucleic acid molecule". The nucleotides can be ribonucleotides, deoxyribonucleotides, or modified forms of either type of nucleotide (e.g. as described below for antisense nucleotide molecules). The term includes single and double stranded forms of DNA or RNA. DNA includes, for example, cDNA, genomic DNA, chemically synthesized DNA, DNA amplified by PCR, and combinations thereof. The polynucleotides of the invention include full-length genes and cDNA molecules as well as fragments thereof.

Variants can be prepared, for example, by substituting, deleting or adding one or more amino acid residues in the amino acid sequence of a native CXCL10 polypeptide or CXCR3 polypeptide or fragment thereof, and screening for biological activity. Preferably, substitutions are made with conservative amino acid residues, i.e., residues having similar physical, biological or chemical properties.

A peptidomimetic is a compound that mimics the conformation and certain stereochemical features of the biologically active form of a particular peptide. In general, peptidomimetics are designed to mimic certain desirable properties of a compound, but not the undesirable properties, such as flexibility, that lead to a loss of a biologically active conformation and bond breakdown. Peptidomimetics may be prepared from biologically active compounds by replacing certain groups or bonds that contribute to the undesirable properties with bioisosteres. Bioisosteres are known to those of skill in the art. For example the methylene bioisostere $CH_2S$ has been used as an amide replacement in enkephalin analogs (see, e.g., Spatola (1983) pp. 267-357 in *Chemistry and BIochemistry of Amino Acids, Peptides, and Proteins*, Weistein, Ed. volume 7, Marcel Dekker, New York). By way of illustration, morphine is a well-known peptidomimetic of the peptide endorphin. For purposes herein, cyclic peptides are included among pepidomimetics.

As used herein, "biological activity" includes any parameter that is indirectly or directly under the influence of CXCL10 polypeptide or CXCR3 polypeptide expressed either endogenously or exogenously. It includes binding to a binding partner and regulating the immune response and local inflammation e.g. by regulating T-cell recruitment and adhesion).

A variant of CXCL10 polypeptide may be used, for example, in a screening assay for identifying compounds that inhibit interaction between CXCL10 polypeptide and CXCR3 polypeptide. In that context, the CXCL10 polypeptide variant must be capable of binding CXCR3 polypeptide.

A variant of CXCR3 polypeptide that binds to CXCL10 polypeptide can be used, for example, as an inhibitor of CXCL10 polypeptide or in a screening assay for identifying compounds that inhibit interaction between CXCR3 polypeptide and CXCL10 polypeptide. For example, a fragment of CXCR3 polypeptide comprising the extracellular domain of CXCR3 polypeptide and which can bind CXCL10 polypeptide may be useful as an inhibitor,of CXCL10 polypeptide or as a binding partner in assays for identifying an inhibitor binding of CXCL10 polypeptide to CXCR3 polypeptide.

CXCL10 polypeptide can be conveniently detected in a biological sample (e.g. for practicing the diagnostic methods of the invention) using standard techniques, including for example: ELISA; cytometric bead array (CBA); FACS (i.e. intracellular fluorescence staining); ELIspot; immunoblotting (i.e. western blotting); and microarray.

In the present context, the term "biological sample" denotes any sample obtained from an animal, including for example, tissue, secretion, hair, blood, blood cells (e.g. lymphocytes, such as T-cells) and plasma.

There are many ways in which the CXCL10:CXCR3 axis can be inhibited for treating or ameliorating a respiratory illness in a patient, including for example administering to the patient:
(a) a binding partner of CXCL10 polypeptide or CXCR3 polypeptide;
(b) an antibody that binds CXCL10 polypeptide, CXCR3 polypeptide, or IFN-gamma;
(c) an antisense RNA that that binds to an mRNA encoding CXCL10 polypeptide, CXCR3 polypeptide, or IFN-gamma;
(d) an RNAi that targets mRNA encoding CXCL10 polypeptide, CXCR3 polypeptide, or IFN-gamma;

(e) a transcription regulator protein that inhibits expression of CXCL10 polypeptide, CXCR3 polypeptide or INF-gamma; and (f) a small molecule that interacts with CXCL10 polypeptide, CXCR3 polypeptide, or IFN-gamma or inhibits expression thereof.

Homology/Hybridization

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with any of the sequences identified herein for CXCL10 polypeptides, CXCR3 polypeptides and the polynucleotides encoding them.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, or at least 95%. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

Antisense Nucleic Acid Molecules

Antisense molecules and ribozymes for exogenous administration can be used to effect the degradation and/or inhibition of the translation of a target mRNA involved in the CXCL10:CXCR3 axis, e.g. a mRNA encoding CXCL10 polypeptide. Examples of therapeutic antisense oligonucleotide applications, incorporated herein by reference, include: U.S. Pat. No. 5,135,917, issued Aug. 4, 1992; U.S. Pat. No. 5,098,890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S. Pat. No. 5,286,717 issued Feb. 15, 1994; U.S. Pat. No. 5,276,019 and U.S. Pat. No. 5,264,423; BioWorld Today, Apr. 29, 1994, p. 3.

Preferably, in antisense molecules, there is a sufficient degree of complementarity to the target mRNA to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target mRNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme polynucleotides that may be used to provide the antisense molecules used to practice the invention is disclosed in U.S. Pat. No. 5,932,435 (which is incorporated herein by reference).

Antisense molecules (oligonucleotides) used to practice the invention may include those which contain intersugar backbone linkages such as phosphotriesters, methyl phosphonates, short chain alkyl or cycloalkyl intersugar linkages or short chain heteroatomic or heterocyclic intersugar linkages, phosphorothioates and those with $CH_2$—NH—O—$CH_2$, $CH_2$—$N(CH_3)$—O—$CH_2$ (known as methylene(methylimino) or MMI backbone), $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—P—O—$CH_2$). Oligonucleotides having morpholino backbone structures may also be used (U.S. Pat. No. 5,034,506). In alternative embodiments, antisense oligonucleotides may have a peptide nucleic acid (PNA, sometimes referred to as "protein nucleic acid") backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., 1991, Science 254:1497 and U.S. Pat. No. 5,539,082). The phosphodiester bonds may be substituted with structures which are chiral and enantiomerically specific. Persons of ordinary skill in the art will be able to select other linkages for use in practice of the invention.

Antisense oligonucleotides may also include species which include at least one modified nucleotide base. Thus, purines and pyrimidines other than those normally found in nature may be used. Similarly, modifications on the pentofuranosyl portion of the nucleotide subunits may also be effected. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_n$ $NH_2$ or $O(CH_2)_n$ $CH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

In some embodiments, the antisense oligonucleotides used to practice the invention may comprise from about 5 to about 100 nucleotide units. In many cases, the antisense oligonucleotide used to practice the invention comprises at least 14, 16 or 30 contiguous nucleotides or modified nucleotides that are complementary to a contiguous sequence of nucleotides encoding the target polypeptide (e.g. CXCL10 polypeptide). As will be appreciated, a nucleotide unit is a base-sugar combination (or a combination of analogous structures) suitably bound to an adjacent nucleotide unit through phosphodiester or other bonds forming a backbone structure.

RNAi

In a further embodiment, the present invention relates to the use of RNA interference (RNAi) technology, a type of post-transcriptional gene silencing, for treating respiratory illnesses (e.g. community-acquired pneumonia and SARS). RNAi may be used to create a pseudo "knockout", i.e. a system in which the expression of the product encoded by a gene or coding region of interest is reduced, resulting in an overall reduction of the activity of the encoded product in a system. As such, RNAi may be used to target a polynucleotide, to in turn reduce its expression and the level of activity of the product which it encodes (i.e. a polypeptide involved in the CXCL10:CXCR3 axis). Such a system may be used for functional studies of the product, as well as to treat disorders related to the activity of such a product. RNAi is described in for example Hammond et al. (2001) Nature Rev. Genet. 2: 110-1119; Sharp (2001) Genes Dev. 15: 485-490; Caplen et al. (2001), Sedlak (2000) and published US patent applications 20020173478 (Gewirtz; published Nov. 21, 2002) and 20020132788 (Lewis et al.; published Nov. 7, 2002), all of which are herein incorporated by reference. Reagents and kits for performing RNAi are available commercially from for example Ambion Inc. (Austin, Tex., USA) and New England Biolabs Inc. (Beverly, Mass., USA).

The initial agent for RNAi in some systems is thought to be dsRNA molecule corresponding to a target polynucleotide. The dsRNA is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the RNase III family of dsRNA-specific ribonucleases. Alternatively, RNAi may be effected via directly introducing into the cell, or generating within the cell by introducing into the cell a suitable precursor (e.g. vector encoding precursor(s), etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA or siRNA-like molecules into cells. RNAi may for example be performed using chemically-synthesized RNA (Brown et al., 2002). Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using E. coli RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods are described in for example Brummelkamp et al. (2002), Lee et al. (2002), Miyagashi and Taira (2002), Paddison et al. (2002) Paul et al. (2002) Sui et al. (2002) and Yu et al. (2002). Various methods for introducing such vectors into cells, either in vitro or in vivo (e.g. gene therapy) are known in the art.

Accordingly, expression of CXCL10 polypeptide may be inhibited by introducing into or generating within a cell an siRNA or siRNA-like molecule corresponding to a polynucleotide encoding either CXCL10 polypeptide or an inducer of CXCL10 polypeptide expression (such as IFN-γ), or to an polynucleotide homologous thereto. "siRNA-like molecule" refers to a polynucleotide molecule similar to an siRNA (e.g. in size and structure) and capable of eliciting siRNA activity, i.e. to effect the RNAi-mediated inhibition of expression. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecule is about 21-23 nucleotides in length. In an embodiment, siRNA or siRNA-like molecule comprises a 19-21 bp duplex portion, each strand having a 2 nucleotide 3' overhang. In embodiments, the siRNA or siRNA-like molecule is substantially identical to a polynucleotide encoding either CXCL10 polypeptide or an inducer of CXCL10 polypeptide expression (such as IFN-γ). In embodiments, the sense strand of the siRNA or siRNA-like molecule is substantially identical to the coding sequence for human CXCL10 polypeptide mRNA (as set forth in GenBank accession No. NM_001565).

Polypeptide Production and Purification

Recombinant full-length human and murine CXCL10 polypeptide (IP-10) are available commercially for example from BIODESIGN International.

Polypeptides used to practice the invention can also be prepared for example by culturing host cells that have been transformed or injected with polynucleotides encoding them (or vectors comprising such polynucleotides), under culture conditions suitable to express the polypeptide. The polypeptide so expressed may then be purified from such culture using known purification processes, such as gel filtration and ion exchange chromatography. The purification of the polypeptide may also include an affinity column containing agents which will bind to the polypeptide (e.g. an anti-CXCL10 polypeptide or anti-CXCR3 polypeptide antibody); one or more column steps over such affinity resins as concanavalin A-agarose, heparin-toyopearl®or Cibacrom blue 3GA Sepharose® ; one or more steps involving hydrophobic interaction chromatography using such resins as phenyl ether, butyl ether, or propyl ether; or immunoaffinity chromatography. Alternatively, the polypeptides of interest may also be expressed in a form that will facilitate purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.), and InVitrogen, respectively. The polypeptide can also be tagged with an epitope and subsequently purified by using a specific antibody directed to such epitope. One such epitope ("Flag") is commercially available from Kodak (New Haven, Conn.).

Optionally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can be employed to provide a substantially purified recombinant polypeptide, i.e. a recombinant polypeptide that is substantially free of other mammalian polypeptides and is defined in accordance with the invention as a "substantially purified polypeptide". Polypeptides can also be expressed as a product of transgenic animals, e.g., as a component of the milk of transgenic cows, goats, pigs, or sheep which are characterized by somatic or germ cells containing a polynucleotide encoding the polypeptide.

Suitable host cells for expression of the polypeptide include eukaryotic and prokaryotic cells. Materials and methods for baculovirus/insect cell expression systems are commercially available in kit form from, e.g., Invitrogen, San Diego, Calif., U.S.A. (the MaxBac® kit), as well as methods described in Summers and Smith, Texas Agricultural Experiment Station Bulletin No. 1555 (1987), and Luckow and Summers, *Bio/Technology* 6:47 (1988), incorporated herein by reference. Mammalian host cells include, for example, the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, BHK (ATCC CRL 10) cell lines, the CV1/EBNA cell line derived from the African green monkey kidney cell line CV1 (ATCC CCL 70) (see, McMahan et al. *EMBO J.* 10: 2821, 1991), human kidney 293 cells, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, it may be possible to produce the polypeptide in lower eukaryotes such as yeast or in prokaryotes such as bacteria. Potentially suitable yeast strains include *Saccharomyces cerevisiae, Schizosaccharomyces pombe, Kluyveromyces* strains, *Candida,* or any yeast strain capable of expressing heterologous polypeptides. Potentially suitable bacterial strains include, for example, *Escherichia coli, Bacillus subtilis, Salmonella typhimurium,* or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain the functional polypeptide. Such covalent attachments may be accomplished using known chemical or enzymatic methods. The polypeptide may also be produced by operably linking a polynucleotide encoding it to suitable control sequences in one or more insect expression vectors, and employing an insect expression system.

Cell-free translation systems can also be employed to produce polypeptides using RNAs derived from nucleic acid constructs disclosed herein. A host cell that comprises an isolated polynucleotide used to practice the invention preferably operably linked to at least one expression control sequence, is a "recombinant host cell".

Established methods for introducing DNA into mammalian cells have been described (Kaufman, R. J., *Large Scale Mammalian Cell Culture,* 1990, pp. 15-69). Additional protocols using commercially available reagents, such as Lipofectamine or Lipofectamine-Plus lipid reagent (Gibco/BRL), can be used to transfect cells (Felgner et al., *Proc.*

*Natl. Acad. Sci. USA* 84:7413, 1987). In addition, electroporation can be used to transfect mammalian cells using conventional procedures, such as those in Sambrook et al. (*Molecular Cloning: A Laboratory Manual,* 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487, 1990, describes several selection schemes, such as dihydrofolate reductase (DHFR) resistance. A suitable strain for DHFR selection can be CHO strain DX-B11, which is deficient in DHFR (Urlaub et al., *Proc. Natl. Acad. Sci. USA* 77:4216, 1980). A plasmid expressing the DHFR cDNA can be introduced into strain DX-B11, and only cells that contain the plasmid can grow in the appropriate selective media. Other examples of selectable markers that -can be incorporated into an expression vector include cDNAs conferring resistance to antibiotics, such as G418 and hygromycin B. Cells harboring the vector are selected on the basis of resistance to these compounds.

It is also possible to utilize an affinity column having an affinity moeity (such as a monoclonal antibody generated against either CXCL10 polypeptide or CXCR3 polypeptide) to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention. In this aspect of the invention, the affinity moeity (e.g., an antibody that binds CXCL10 polypeptide or CXCR3 polypeptide) can be bound to a solid phase support or a similar substrate suitable for identifying, separating, or purifying cells that express polypeptides on their surface. Adherence of the binding protein to the solid phase surface can be accomplished by any means, for example, magnetic microspheres can be coated with these binding proteins and held in the incubation vessel through a magnetic field. Suspensions of cell mixtures are contacted with the solid phase that has such binding proteins thereon. Binding proteins bind those cells having target polypeptides vention on their surface, and unbound cells (e.g., cells lacking target polypeptide) are washed away from the bound cells. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. Alternatively, mixtures of cells suspected of containing cells expressing polypeptides of interest are first incubated with a biotinylated binding partner. Incubation periods are typically at least one hour in duration to ensure sufficient binding to polypeptides. The resulting mixture then is passed through a column packed with avidin-coated beads, whereby the high affinity of biotin for avidin provides the binding of the cells to the beads. Use of avidin-coated beads is known in the art (see, Berenson, et al. *J. Cell. Biochem.,* 10D:239, 1986). Wash of unbound material and the release of the bound cells is performed using conventional methods.

Polypeptides used to practice the invention may also be produced by known conventional chemical synthesis. Methods for constructing the polypeptides by synthetic means are known to those skilled in the art. The synthetically-constructed polypeptide sequences, by virtue of sharing primary, secondary or tertiary structural and/or conformational characteristics with a native polypeptides may possess biological properties in common therewith, including biological activity. Thus, the synthesized polypeptides may be employed as biologically active or immunological substitutes for natural, purified polypeptides in screening of therapeutic compounds and in immunological processes for the development of antibodies.

The desired degree of purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational. processing, and the like. Most preferably, the polypeptide used to practice the invention is purified to substantial homogeneity, as indicated by a single polypeptide band upon. analysis by SDS-PAGE. The polypeptide band can be visualized by silver staining, Coomassie blue staining, or (if the polypeptide is radiolabeled) by autoradiography.

Antibodies

Antibodies that bind CXCL10 polypeptide or the extracellular domain of CXCR3 polypeptide can be used to practice the methods of the invention. Specifically, such antibodies can be used in methods for diagnosing respiratory illnesses (e.g. community-acquired pneumonia and SARS) and for monitoring the course of treatment and determining the prognosis of a patient suffering from respiratory illnesses.

Antibodies that bind CXCL10 polypeptide or the extracellular domain of CXCR3 polypeptide are also useful as binding partners for CXCL10 polypeptide in screening methods of the invention.

Antibodies that bind CXCL10 polypeptide or the extracellular domain of CXCR3 polypeptide are also useful for treating respiratory illnesses and in the preparation of medicaments and pharmaceutical compositions therefor.

Anti-CXCR3 polypeptide antibodies can be used for example for screening for host cells that express CXCR3 polypeptides or for affinity purification of CXCR3 polypeptides.

R & D Systems (http://www.rndsystems.com/) supplies anti-murine and anti-human CXCL10 polypeptide and CXCR3 polypeptide antibodies and related reagents useful for laboratory ELISAs.

Antibodies used to practice the invention may be either polyclonal or monoclonal. Antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monoclonal antibodies may also be in the form of immunoglobulin fragments, e.g., F(ab)'$_2$, Fab or Fab' fragments. The antibodies used to practice the invention are of any isotype, e.g., IgG or IgA, and polyclonal antibodies are of a single isotype or a mixture of isotypes.

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{13}$I, $^{35}$S or $^{3}$H.

Accordingly, a further aspect of the invention provides a diagnostic method for detecting the presence of a CXCL10 polypeptide and/or activity in a tissue or body fluid, by contacting the tissue or body fluid with an anti-CXCL10 polypeptide antibody such that an immune complex is formed, and by detecting such complex to indicate the presence of the CXCL10 polypeptide and/or activity in the sample or the organism from which the sample is derived. The tissue or body fluid sample can be obtained from a mammal suspected of being infected with respiratory illnesses.

Those skilled in the art will readily understand that the immune complex is formed between a component of the sample and the antibody, and that any unbound material can be removed prior to detecting the complex. It is understood that diagnostic method of the invention may be used for screening a sample, such as, for example, blood, plasma, lymphocytes, cerebrospinal fluid, urine, saliva, epithelia, fibroblasts, or a host cell, for the presence of a CXCL10 polypeptide.

For diagnostic applications, the antibody may be either in a free state or immobilized on a solid support, such as a tube, a bead, or any other conventional support used in the field. Immobilization may be achieved using direct or indirect means. Direct means include passive adsorption (non-covalent binding) or covalent binding between the support and the reagent. By "indirect means" is meant that an anti-reagent compound that interacts with a reagent is first attached to the solid support. Indirect means may also employ a ligand-receptor system, for example, where a molecule such as a vitamin is grafted onto the reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent can be labeled with a detection means which allows for the detection of the reagent when it is bound to its target. Suitable detection means include for example fluorescent agents such as fluorescein isocyanate or fluorescein isothiocyanate, enzymes such as horse radish peroxidase or luciferase or alkaline phosphatase, and radioactive elements such as $^{125}$I or $^{51}$Cr.

In a preferred embodiment, the CXCL10 polypeptide assay is a cytometric bead array (CBA) assay. CBA assays are commercially available, e.g. from Becton Dickinson.

For use in a purification, the antibody is either polyclonal or monoclonal, and preferably is of the IgG type. Purified IgGs are prepared from an antiserum using standard methods (see, e.g., Coligan et al. (1994) supra). Conventional chromatography supports, as well as standard methods for grafting antibodies, are described in, e.g., Antibodies: A Laboratory Manual, Harlow and Lane (eds.) Cold Spring Harbour Laboratory Press (1988), herein incorporated by reference, and outlined below.

Briefly, the sample, preferably in a buffer solution, is applied to a chromatography material, preferably equilibrated with the buffer used to dilute the sample so that the polypeptide used to practice the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

A further aspect of the present invention is a diagnostic imaging method for diagnosing respiratory illness, which comprises introducing into a biological system an anti-CXCL10 polypeptide antibody which is used in conjunction with an appropriate detection system to identify areas where CXCL10 polypeptide or its activity is present or absent.

A further aspect of the present invention provides therapeutic applications of antibodies, whereby antibodies that bind CXCL10 polypeptide, CXCR3 polypeptide, or IFN-γ are administered to a patient to treat or ameliorate respiratory illnesses by downregulating or inhibiting the CXCL10:CXCR3 axis.

Screening Assays

Another aspect of the invention relates to the use of CXCL10 polypeptide or CXCR3 polypeptide as a target in screening assays that may be used to identify a therapeutic agent for treating respiratory illnesses.

In some embodiments, such a screening assay may comprise the steps of:
(a) providing a test compound;
(b) providing a polypeptide selected from CXCL10 polypeptide and CXCR3 polypeptide; and
(c) detecting whether the test compound binds to said polypeptide.

Another type of assay for identifying a inhibitor of interaction between CXCL10 polypeptide and CXCR3 polypeptide is a competitive binding assay, utilizing a "binding partner" of between CXCL10 polypeptide or CXCR3 polypeptide. Such a screening assay may comprise the steps of:
(a) providing a test compound;
(b) providing a polypeptide selected from between CXCL10 polypeptide and CXCR3 polypeptide;
(c) providing a source of a binding partner that binds to said polypeptide; and
(d) detecting whether the test compound inhibits interaction between said binding partner and said polypeptide.

Binding partners that bind to between CXCL10 polypeptide and CXCR3 polypeptide include for example antibodies and polypeptides. For example, suitable binding partners for CXCL10 polypeptide include a polypeptide comprising the extracellular domain of CXCR3 polypeptide that is capable of binding CXCL10 polypeptide.

Binding of the binding partner to CXCL10 polypeptide can be determined by conventional methods, for example by measuring release of a radiolabelled binding partner or by measuring CXCL10 polypeptide activity (e.g. binding to anti-CXCL10 polypeptide antibodies or CXCR3 polypeptide).

Test compounds include, for-example, 1) peptides such as soluble peptides, including Ig-tailed fusion peptides and members of random peptide libraries (see, e.g., Lam et al., Nature 354:82-84 (1991); Houghten et al., Nature 354:84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767-778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries), including peptidomimetics.

Compounds that may be useful for inhibiting CXCL10 polypeptide activity, in vivo or in vitro, by binding thereto include for example: polypeptides comprising the extracellular domain of CXCR3 polypeptide; and anti-CXCL10 polypeptide antibodies.

In another aspect, the invention provides a reporter assay-based method of selecting agents which inhibit expression of CXCL10 polypeptide or CXCR3 polypeptide, i.e. for use in identifying a compound for the treatment of respiratory illnesses. Such a method may comprise assaying expression of CXCL10 polypeptide or CXCR3 polypeptide in the presence versus the absence of a test compound. Such gene expression may be measured by detection of the corresponding RNA or protein, or via the use of a suitable reporter construct comprising a transcriptional regulatory element(s) normally associated with the gene encoding CXCL10 polypeptide or CXCR3 polypeptide, operably-linked to a reporter gene. The expression of such a reporter gene may be measured on the transcriptional or translational level, e.g. by the amount of RNA or protein produced. RNA may be detected by for example Northern analysis or by the reverse transcriptase-polymerase chain reaction (RT-PCR) method (see for example Sambrook et al (1989) Molecular Cloning: A Laboratory Manual (second edition), Cold Spring Harbor Laboratory Press, Cold Spring Harbor, N.Y., USA). Protein levels may be detected either directly using affinity reagents (e.g. an antibody or fragment thereof [for methods, see for example Harlow, E. and Lane, D (1988) *Antibodies: A Laboratory Manual*, Cold Spring Harbor Laboratory Press, Cold Spring Harbor, N.Y.]; a ligand which binds the protein) or by other properties (e.g. fluorescence in the case of green fluorescent protein) or by measurement of the protein's activity, which may entail enzymatic activity to produce a detectable product (e.g. with altered spectroscopic properties) or a detectable phenotype (e.g. alterations in cell growth). Suitable reporter genes include but are not limited to chloramphenicol acetyltransferase, beta-D galactosidase, luciferase, or green fluorescent protein.

Mention is made of VERO 6 cells, which express CXCL10 polypeptide when infected with SARS CoV, and U937 cells, which express CXCL10 polypeptide when induced with IFN-γ, as examples of cells that can be used in the present methods for identifying compounds that inhibit expression of CXCL10 polypeptide.

Inhibitors of CXCL10 polypeptide expression include for example antibodies that bind to IFN-γ, which is known to induce CXCL10 polypeptide expression in certain cell types.

These screening methods can be used to identify compounds that inhibit the biological activity of CXCL10 polypeptide and/or CXCR3 polypeptide. These assays may further comprise a step of assaying the compounds so identified for their ability to inhibit the CXCL10:CXCR3 axis in a biological system, e.g. by assaying for inhibition of inflammation and injury in the lungs of a SARS model animal such as a mouse or a monkey.

The above-noted methods and assays may be employed either with a single test compound or a plurality or library (e.g. a combinatorial library) of test compounds. In the latter case, synergistic effects provided by combinations of compounds may also be identified and characterized. The above-mentioned compounds may be used for inhibiting the activity of the CXCL10:CXCR3 axis, i.e. for treatment of respiratory illness in a patient, or may be used as lead compounds for the development and testing of additional compounds having improved specificity, efficacy and/or pharmacological (e.g. pharmacokinetic) properties.

In certain embodiments, one or a plurality of the steps of the screening/testing methods of the invention may be automated. Such assay systems may comprise a variety of means to enable and optimize useful assay conditions. Such means may include but are not limited to: suitable buffer solutions, for example, for the control of pH and ionic strength and to provide any necessary components for optimal CXCL10 polypeptide or CXCR3 polypeptide activity and stability (e.g. protease inhibitors), temperature control means for optimal a CXCL10 polypeptide or CXCR3 polypeptide activity and or stability, and detection means to enable the detection of CXCL10 polypeptide activity. A variety of such detection means may be used, including but not limited to one or a combination of the following: radiolabelling (e.g. $^{32}p$), antibody-based detection, fluorescence, chemiluminescence, spectroscopic methods (e.g. generation of a product with altered spectroscopic properties), various reporter enzymes or proteins (e.g. horseradish peroxidase, green fluorescent protein), specific binding reagents (e.g. biotin/streptavidin), and others. Binding may also be analysed using generally known methods in this area, such as electrophoresis on native polyacrylamide gels, as well as fusion protein-based assays such as the yeast 2-hybrid system or in vitro association assays, or proteomics-based approachs to identify CXCL10 polypeptide binding proteins.

The assay may be performed in vitro using cell-based or cell-free systems as a source of CXCL10 polypeptide or CXCR3 polypeptide. Such assays may be performed in an array format. One or more assay steps can be automated.

To perform cell free drug screening assays, it is sometimes desirable to immobilize either the CXCL10 polypeptide or CXCR3 polypeptide or the binding partner, to facilitate separation of complexes from uncomplexed forms of one or both components, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase (GST) fusion proteins can be adsorbed onto glutathione sepharose beads (Sigma Chemical, St. Louis, Mo.) or glutathione derivatized microtitre plates, which are then combined with the cell lysates (e.g., 35 S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of CXCL10 polypeptide or CXCR3 polypeptide found in the bead fraction quantitated from the gel using standard electrophoretic techniques. For example, either the CXCL10 polypeptide or its target molecule can be immobilized utilizing conjugation of biotin and streptavidin using techniques well known in the art (biotinylation kits and streptavidin-coated 96-well plates are commercially available e.g. from Pierce Chemicals, Rockford Ill.). Alternatively, antibodies reactive with the CXCL10 polypeptide or CXCR3 polypeptide but which do not interfere with binding of the polypeptide to its target molecule can be derivatized to the wells of the plate, and the protein trapped in the wells by antibody conjugation. Preparations of a binding partner and a test compound are incubated in the wells presenting CXCL10 polypeptide or CXCR3 polypeptide and the amount of complex trapped in the well can be quantitated. Methods for detecting such complexes, in addition to those described above for the GST-immobilized complexes, include immunodetection of complexes using antibodies, as well as enzyme-linked assays which rely on detecting an enzymatic activity associated with the complex (e.g. horseradish peroxidase, alkaline phosphatase, or luciferase).

In one embodiment, the test compound is labeled. Either the test compound, or the binding partner, or both, is added first to a CXCL10 polypeptide or CXCR3 polypeptide for a time sufficient to allow binding. Incubations may be performed at any temperature which facilitates optimal activity, typically between 4 and 40 degrees C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

The interaction between two molecules can also be detected, e.g., using a fluorescence assay in which at least one molecule is fluorescently labeled. One example of such an assay includes fluorescence energy transfer (FET or FRET for fluorescence resonance energy transfer) (see, for example, Lakowicz et al., U.S. Pat. No. 5,631,169; Stavrianopoulos, et al., U.S. Pat. No. 4,868,103). Another example of a fluorescence assay is fluorescence polarization (FP) (see, e.g., Nasir et al. (1999) *Comb Chem HTS* 2:177-190; Jameson et al. (1995) *Methods Enzymol* 246:283; Seethala et al. (1998) *Anal Biochem.* 255:257), which can be monitored in multiwell plates, e.g., using the Tecan Polarion™ reader (see, e.g., Parker et al. (2000) *Journal of Biomolecular Screening* 5 :77-88; and Shoeman, et al. (1999) 38, 16802-16809).

The ability of a binding partner to bind to a CXCL10 polypeptide or CXCR3 polypeptide can also be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). Agents that inhibit CXCL10 polypeptide or CXCR3 polypeptide can be identified using one or more of the above assays, alone or in combination. It is generally preferable to use a cell-based or cell free system first and then confirm activity in a model system such as an animal, e.g. using a mammal (such as a mouse, rat, primate or other non-human). Thus, the above-described assay methods may further comprise determining whether any compounds so identified can be used for treating SARS, such as examining their effect(s) on disease symptoms in suitable disease animal model systems. The above-mentioned methods may similarly be used to identify and characterize compounds for the inhibition of CXCL10 polypeptide or CXCR3 polypeptide in a biological system, e.g. a whole-animal system such as mouse or monkey.

In another embodiment, polynucleotides encoding CXCL10 polypeptides or CXCR3 polypeptide can be used in a yeast two-hybrid system to identify other protein partner pairs of CXCL10 polypeptide or CXCR3 polypeptide.

Therapeutic Formulations

In various embodiments, inhibitors of CXCL10 polypeptide or CXCR3 polypeptide activity may be used therapeutically in formulations or medicaments to treat SARS in a subject such as mammalian subject. The terms "treat", "treating" and "treatment" used herein include curative, preventative (e.g. prophylactic) and palliative or ameliorative treatment. The invention provides corresponding methods of medical treatment, in which a therapeutic dose of an inhibitor of CXCL10 polypeptide or CXCR3 polypeptide is administered in a pharmacologically acceptable formulation, e.g. to a patient or subject in need thereof.

Accordingly, the invention also provides therapeutic compositions comprising a compound capable of inhibiting CXCL10 polypeptide or CXCR3 polypeptide activity and a pharmacologically acceptable excipient or carrier. In one embodiment, such compositions include an inhibitor of CXCL10 polypeptide or CXCR3 polypeptide in a therapeutically or prophylactically effective amount sufficient to treat respiratory illnesses. The therapeutic composition may be soluble in an aqueous solution at a physiologically acceptable pH.

Inhibitors of the CXCL10:CXCR3 axis that may be used as therapeutic agents include for example:

(a) a binding partner of CXCL10 polypeptide or CXCR3 polypeptide;

(b) an antibody that binds CXCL10polypeptide, CXCR3 polypeptide, or IFN-gamma;

(g) an antisense RNA that that binds to an mRNA encoding CXCL10 polypeptide, CXCR3 polypeptide, or IFN-gamma;

(h) an RNAi that targets mRNA encoding CXCL10 polypeptide, CXCR3 polypeptide, or IFN-gamma;

(i) a transcription regulator protein that inhibits expression of CXCL10 polypeptide, CXCR3 polypeptide or INF-gamma; and (j) a small molecule that interacts with CXCL10 polypeptide, CXCR3 polypeptide, or IFN-gamma or inhibits expression thereof, as can be identified using the methods described herein.

A "therapeutically effective amount" refers to an amount effective, at dosages and for periods of time necessary, to achieve the desired therapeutic result, such as a inhibition of CXCL10 polypeptide or CXCR3 polypeptide activity and in turn a reduction in SARS disease progression. The therapeutically effective amount of inhibitor of CXCL10 polypeptide or CXCR3 polypeptide may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as inhibiting the rate of SARS disease progression. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, a therapeutic agent can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, a therapeutice agent may be formulated with one or more additional compounds that enhance the solubility of the agent.

In accordance with another aspect of the invention, therapeutic compositions of the present invention, comprising an inhibitor of CXCL10 polypeptide CXCL10 polypeptide or CXCR3 polypeptide, may be provided in containers or commercial packages which further comprise instructions for use of the pharmaceutical composition for treatment of respiratory illnesses.

Accordingly, the invention further provides a commercial package comprising an inhibitor of CXCL10 polypeptide or CXCR3 polypeptide or the above-mentioned composition together with instructions for the treatment of respiratory illnesses. The invention further provides a use of an inhibitor of CXCL10 polypeptide CXCL10 polypeptide or CXCR3 polypeptide for treatment of respiratory illnesses. The invention further provides a use of an inhibitor of CXCL10 polypeptide CXCL10 polypeptide or CXCR3 polypeptide in the preparation of a medicament for treatment of respiratory illnesses.

All publications, patent applications, patents and other references mentioned herein are hereby incorporated by reference in their entirety.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to".

The following examples are illustrative of various aspects of the invention, and do not limit the broad aspects of the invention as disclosed herein.

EXAMPLES

Materials and Methods

Patients

Study subjects were enrolled without bias to age, sex or previous medical history Informed consent was obtained from all subjects under the approval of the Research Ethics Boards of the University Health Network and participating hospitals. Clinical details were provided to us following completion of our analysis and can be found in other studies describing this overlapping patient cohort (3,5,12,13). Our cohort consisted of 63 confirmed SARS patients (median age 40 years, 23 males and 40 females) as defined by Health Canada case definitions (Health Canada: Severe acute respiratory syndrome (SARS), http://www.sars.gc.ca). These patients were identified with early clinical presentation of SARS symptoms, radiographic evidence consistent with SARS and laboratory evidence of SARS-associated CoV infection (positive PCR, seroconversion and/or virus isolation results). SARS patients were treated similarly with steroids (approx. 20 to 50 mg/d hydrocortisone for 10-14 d, not beginning within 48 h from onset of symptoms) during their disease course, however 10 critical SARS patients required intubation, admission to the intensive care unit (ICU) and longer periods of steroid treatment. Three of these SARS patients died in the ICU during our study and right and left lower lung samples were obtained during autopsy.

Recovered SARS patients, i.e. those taken off supplemental oxygen or steroid therapy or those discharged from the hospital, were termed as convalescents.

Suspect SARS patients (n=80) were also included in our analysis having concurrently presented to emergency rooms or been admitted to hospital with SARS-like symptoms/respiratory ailments during the Toronto outbreaks. Patients in this group (39 males and 41 females with a median age of 42 years) were excluded as SARS when an alternative medical or microbiological diagnosis was found. Lastly, 14 healthy normal volunteers (7 males and 7 females with a median age of 36 years) were sampled.

Ribavirin (5-7 d course at 3-5 d post onset of symptoms) was administered to approx. 20% of SARS patients enrolled in the longitudinal experiments. No significant effects of ribavirin treatment were noted in our analyses.

Patient Sample Collection and Preparation

Peripheral blood was collected in heparinized blood collection tubes from study participants upon onset of SARS-like symptoms, after every five days during hospitalization and at discharge from the hospital. Whole blood RNA was isolated using Qiagen Paxgene RNA kits (Mississauga, ON, Canada). Plasma was obtained by centrifugation. Peripheral blood mononuclear cells (PBMCs) were isolated by density centrifugation. Some PBMCs were cryopreserved using patients' plasma supplemented with 10% DMSO and maintained in liquid nitrogen for use in the proliferation assays.

Cytometric Bead Array (CBA)

Cytokine and chemokine levels were assayed by human CBA kits according to the manufacturer's protocols (BD Biosciences, San Jose, Calif.). Briefly, specific capture beads for cytokines and chemokines were mixed with 50 µl of patient plasma or standards and multiple phycoerythrin-conjugated detection antibodies were added. Following a 3 h incubation period with recombinant protein standards or test samples, samples were fixed with 2% paraformaldehyde and the acquisition of sample data was performed using a two-color flow cytometer. Results were generated in graphical and tabular format using BD CBA Analysis Software.

Real-Time PCR

Total RNA was purified from lung tissues and cells using TriPure Reagent (Roche, Basel, Switzerland) (Mississauga, ON, Canada) according to the manufacturers' specifications. RNA was cleaned up using an RNeasy Purification Kit (Qiagen) and was treated with RNAse-free DNAse on-column treatment to remove genomic DNA (Qiagen). 250 ug mRNA was reverse transcribed into cDNA using SuperScript II (Invitrogen, Burlington, ON, Canada). 0.25 ul cDNA was amplified with the SYBR Green Master Mix (Applied Biosystems, Warrington, UK): 15 min at 95° C. for initial denaturing, followed by 40 cycles of 95° C. for 15 s denaturation step and 60° C. for 1 min annealing/extension step using the ABI 7900 Sequence Detection System (Applied Biosystems). Real-time PCR Primers: CXCL10 F 5'-TCC ACG TGT TGA GAT CAT TGA-3', CXCL10 R 5'-TCT TGA TGG CCT TCG ATT CTG-3', CXCR3 F 5'-GGT GCC CTC TTC AAC ATC AAC-3', CXCR3 R 5'-GGT GGT AGC ATG AAC TAT GTT CAG GTA-3', GAPDH F 5'-GCA CCA CCA ACT GCT TAG CAC-3', GAPDH R 5'-TCT TCT GGG TGG CAG TGA TG-3'. The relative expression of each gene of interest was normalized to GAPDH.

Virus Tissue Culture

Vero E6 cells (American Type Culture Collection, Manassas, Va., USA) were cultured in Dulbecco's Modification of Eagle's Medium supplemented with 1% penicillin/streptomycin and 1% glutamine (Sigma, St. Louis, Mo., USA) and 10% fetal calf serum (Cambrex Corporation, East Rutherford, N.J., USA). Upon confluence (approximately $1-2 \times 10^7$ cells per 162 $cm^2$ flask), cells were infected with 100 p.f.u. of the Tor2 strain of the SARS CoV. At the appropriate time points, media was removed and the cells were washed twice with PBS and removed. Total RNA was purified from the mechanically homogenized cells using TriPure Reagent (Roche).

Proliferation Assay and FACS Analysis

Recombinant SARS CoV N protein was kindly provided by J. Mahony (Hamilton, Canada). $5 \times 10^6$ cryopreserved PBMCs were thawed and labeled with a predetermined concentration of CFSE (Molecular Probes, Eugene, Oreg.). The final concentration of CFSE used for PBMC labeling was 1.5 µM. Cells were washed twice in PBS and resuspended in RPMI media supplemented with 10% human serum. $10^6$/ml CFSE-labeled PBMCs were cultured either in the presence of 2 ug/ml SARS CoV N protein or in media alone. 50 ng/ml SEA (Toxin Technology, Sarasota, Fla.) was used as a positive control (data not shown). After 6 d of in vitro incubation at 37° C. 5% $CO_2$, cells were collected and stained with anti-CD4-APC, anti-CD8-PerCP and anti-CXCR3-PE (BD Biosciences). A minimum of $2-5 \times 10^4$ events, gated on viable $CD4^+$ or $CD8^+$ T cells, were collected on a four colour FACSCalibur™ cytometer and analyzed using FlowJo® software (TreeStar).

SARS Infection of Rhesus and Cynomolgus Macaques

Macaques were housed in an animal BSL-3 facility at the Southern Research Institute in Birmingham, Ala. Rhesus (n=4) and cynomolgus (n=4) macaques were infected with $1 \times 10^6$ p.f.u. SARS-COV (Tor2) intratracheally and monitored for 13 days. Uninfected macaques were used as controls (n=4). Blood samples were collected at day 0, 3, 5, 7 and 13 or whenever containment procedures permitted. PBMCs were isolated by density centrifugation after which RNA was purified using TriPure Reagent as above.

Statistical Methods

Our data was found to be suitable for parametric statistical tests (SigmaStat). Results were compared using Student's t test for unpaired samples and $P<0.05$ was chosen as the level of significance).

Results

In a strategy adopted as a first step in examining dysregulated proinflammatory immune responses as reflected peripherally in SARS-infected patients, we measured plasma levels of cytokines and chemokines by CBA in approximately 700 blood samples taken from consenting confirmed SARS patients, suspect SARS patients (non-SARS, but exhibiting SARS-like symptoms) and healthy controls during the 2003 SARS outbreaks in Toronto, Canada. In general, and as reported in previous studies (14-16), we observed examples of increased expression of proinflammatory cytokine, such as IFN-γ, TNF-α, IL-1β and IL-6, in SARS patients at onset of symptoms relative to healthy controls (data not shown). However, we noted a striking pattern of CXCL10 polypeptide expression in SARS patients of different retrospective severity and outcome of disease, so we focused herein on elucidating the role of the CXCL10:CXCL3 axis in SARS immunopathogenesis.

Firstly, we observed significantly increased levels of CXCL10 polypeptide in the plasma of confirmed SARS patients (mean=4,564 pg/ml) within 48 h of onset of symptoms and under no treatment compared to healthy controls (mean=528 pg/ml) (FIG. 1A). This was the only cytokine or chemokine to show elevated levels in 100% of SARS cases at onset. CXCL10 polypeptide levels were also significantly increased when compared to suspect SARS patients (mean=807 pg/ml) and convalescents (mean=596 pg/ml). Indeed, all patients in the suspect SARS group were excluded as SARS patients when an alternative medical or microbiological diagnosis was found that explained their SARS-like presentation. No confirmed SARS patients had a CXCL10 polypeptide level in plasma of less than 1000 pg/ml, a plateau below which nearly all non-SARS patients and all healthy control levels fell.

Figure 1C:
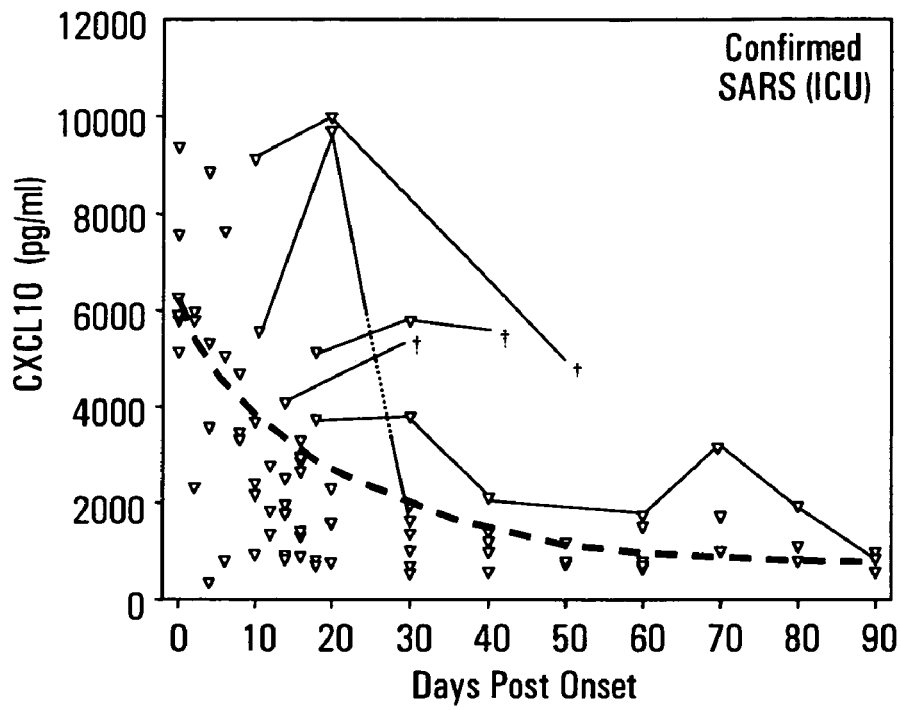

To understand the longitudinal relationship between CXCL10 polypeptide and SARS pathogenesis or disease course we performed a timeline comparison of CXCL10 polypeptide levels in 25 SARS patients with mild to moderate symptoms (FIG. 1B) and 10 severe SARS patients admitted to the ICU and intubated (FIG. 1C). CXCL10 polypeptide levels in non-ICU patients decreased to convalescent levels within 10-12 d (FIG. 1B), whereas the levels in ICU patients (FIG. 1C) remained significantly elevated versus non-ICU SARS patients until at least day 40 ($P<0.05$). The return of CXCL10 polypeptide expression to convalescent levels in mild SARS patients (approx. 10-12 d since onset) and the return of CXCL10 polypeptide expression to convalescent levels in severe SARS patients (approx. 40-50 d since onset) generally correlated with the median duration of SARS illness in mild and severe SARS patients (14 d and 52 d respectively). As described in the *Materials and Methods*, all recovered SARS patients, i.e. those that no longer required supplemental oxygen or steroid therapy before discharge or those discharged from the hospital, were classified as convalescents. Some convalescent patients required lengthy hospital stays ($\geq 90$ d) following their SARS illness due to age or comorbidities.

The highest levels of CXCL10 polypeptide beyond 10 d were recorded in five ICU patients (FIG. 1C, solid lines). Three of these individuals died during the study of complications due to SARS, including an organ transplant recipient on immunosuppression. A fourth critical patient required an unusually lengthy course of steroids before quickly regaining health after day 30. A fifth patient remained in critical condition with protracted SARS infection and ARDS and began to recover at around day 80 in conjunction with CXCL10 polypeptide levels returning to normal. This data indicates that CXCL10 polypeptide is induced early in the course of SARS and continues to be elevated in patients with a poor prognosis.

Figure 1D:
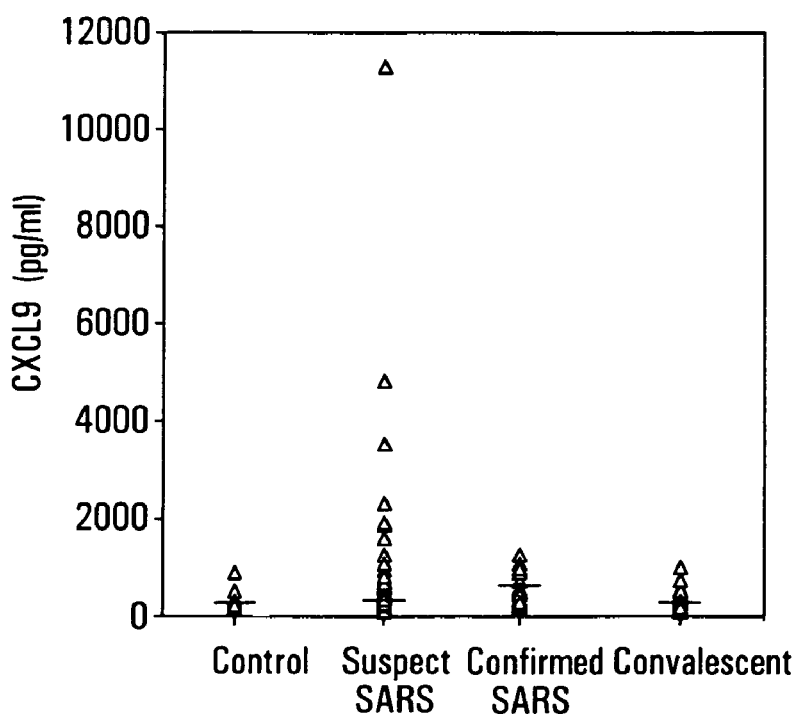
Figure 1E:
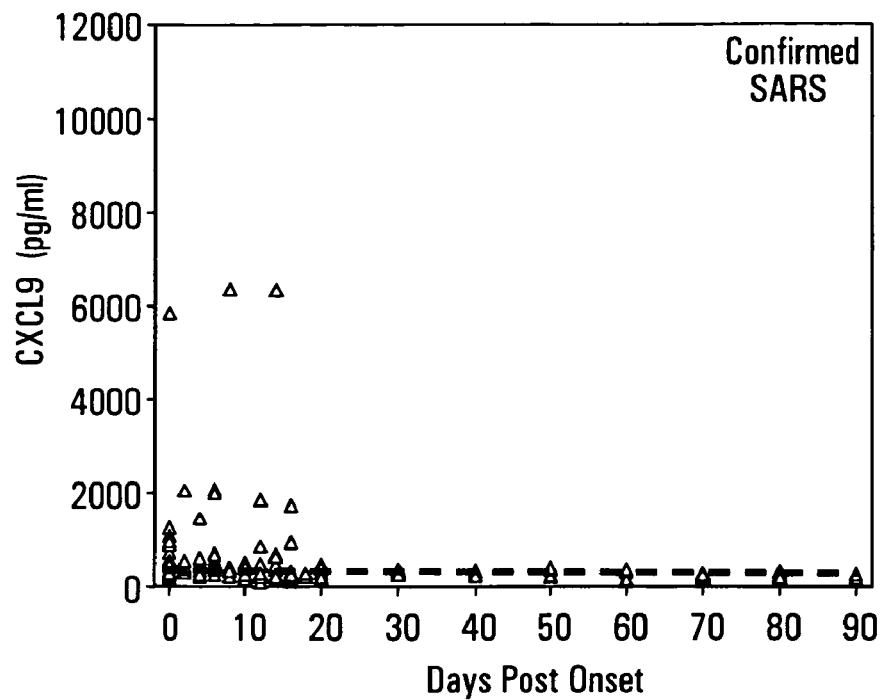
Figure 1F:
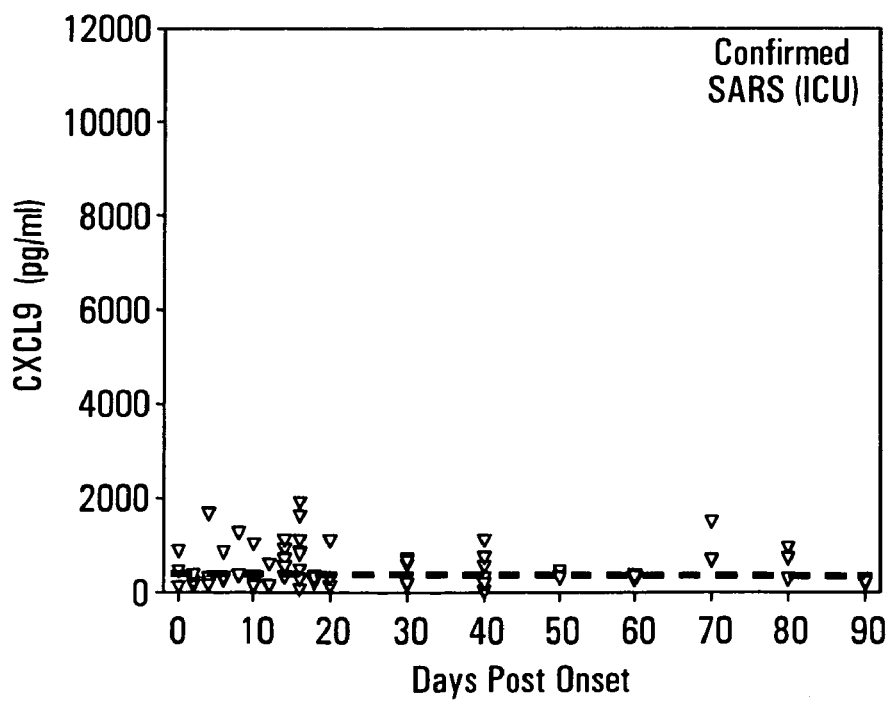

CXCL9 (monokine induced by IFN-γ/MIG) and CXCL10 are non-ELR, CXC chemokines that bind CXCR3 polypeptide and were originally described as being induced by IFN-γ. In contrast to CXCL10 polypeptide, CXCL9 was not significantly increased in the plasma of SARS patients, suspect SARS cases or convalescents (FIG. 1D-F). Also, CXCL8, an ELR CXC chemokine that binds to CXCR1 and CXCR2 mainly expressed on neutrophils, was not significantly expressed in confirmed SARS patients at onset. However, CXCL8 was highly elevated in the plasma of a small subset of SARS patients at 2 to 5 wk from onset of symptoms (data not shown). Interestingly, all of the samples from SARS patients showing highly elevated levels of CXCL8 were obtained from non-ICU SARS patients treated with ribavirin indicating an additional effect of ribavirin treatment (21).

Figure 2A:
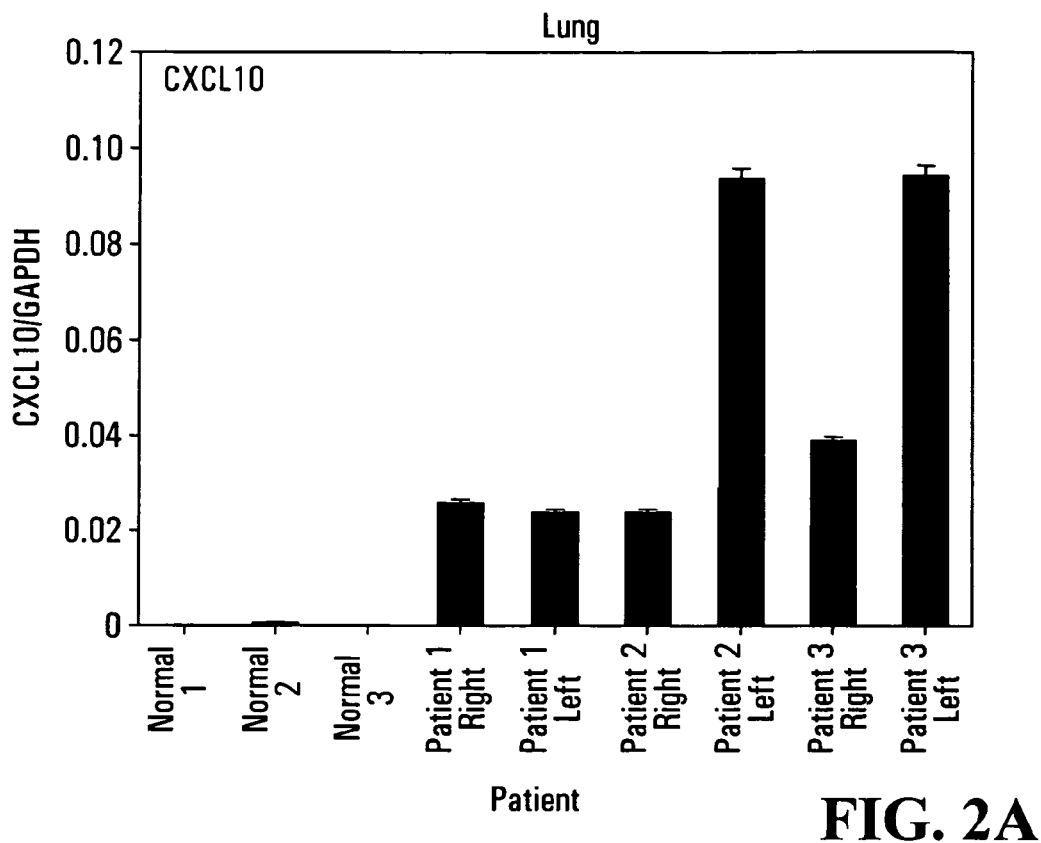
FIG. 2. CXCL10 polypeptide and CXCR3 polypeptide are expressed in the lungs of deceased SARS patients. RNA was isolated from bilateral lower lung biopsies from deceased confirmed SARS patients (n=3) and normal cadaveric lungs (n=3). CXCL10 polypeptide (FIG. 2A) and CXCR3 polypeptide (FIG. 2B) were quantitated by real time PCR. The relative expression of each gene is shown normalized to GAPDH.
Figure 2B:
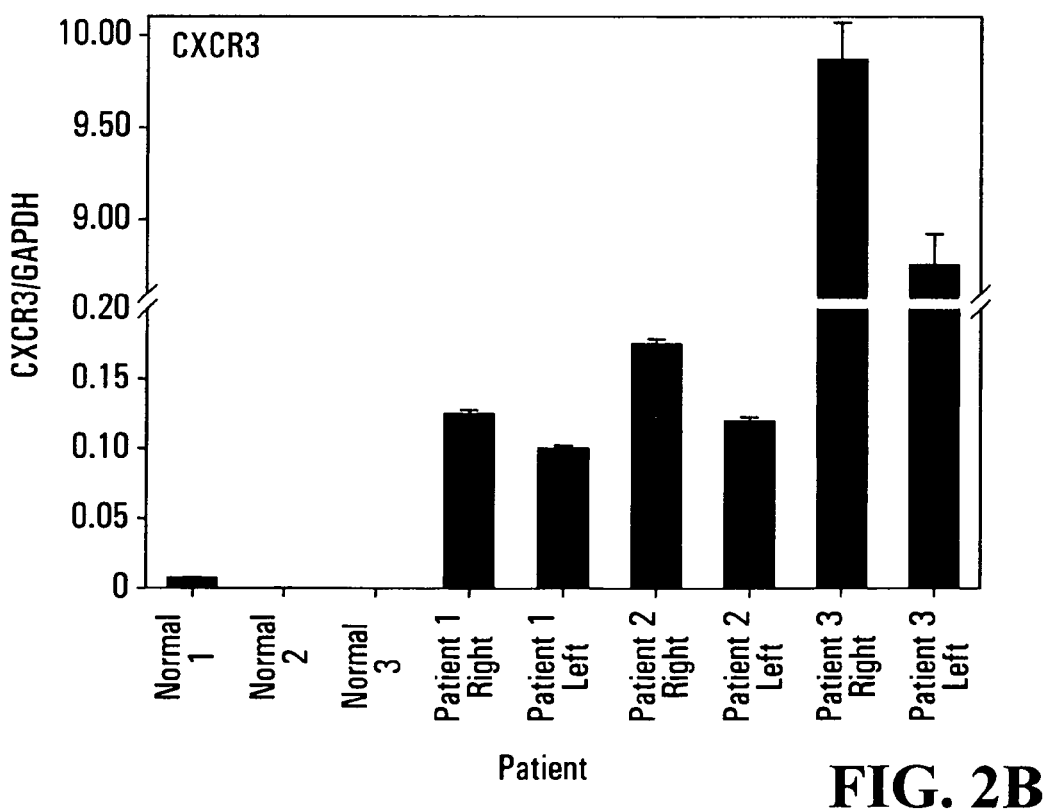
Figure 3A:
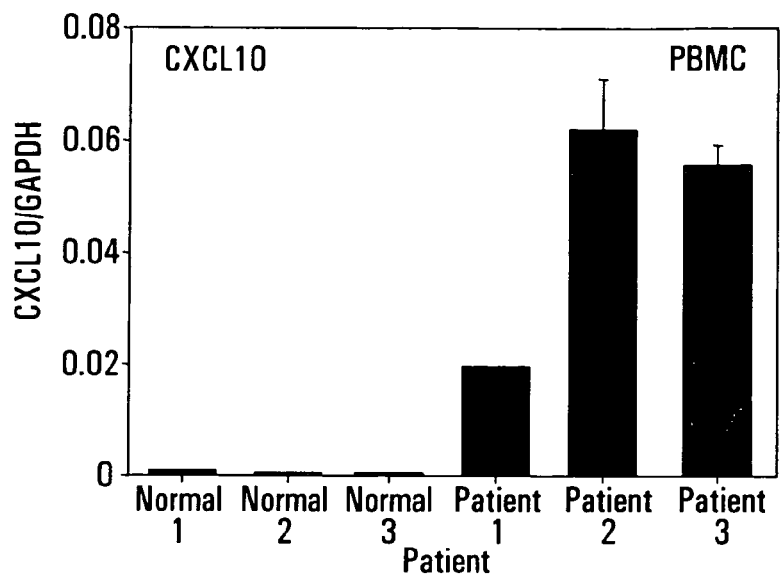
FIG. 3. CXCL10 polypeptide and CXCR3 polypeptide expression by SARS patient PBMCs and CXCL10 polypeptide expression by SARS CoV-infected VERO E6 cells as determined by real time PCR. CXCL10 polypeptide (FIG. 3A) and CXCR3 polypeptide (FIG. 3B) were upregulated in PBMCs from three random SARS patients within 7 days from onset of symptoms in comparison to PBMCs from three healthy controls. CXCL10 polypeptide transcripts were also detected in triplicate cultures of SARS CoV (Tor2)-infected VERO E6 cells at 12-24 hours (FIG. 3C). The relative expression of each gene is shown normalized to GAPDH.
Figure 3B:
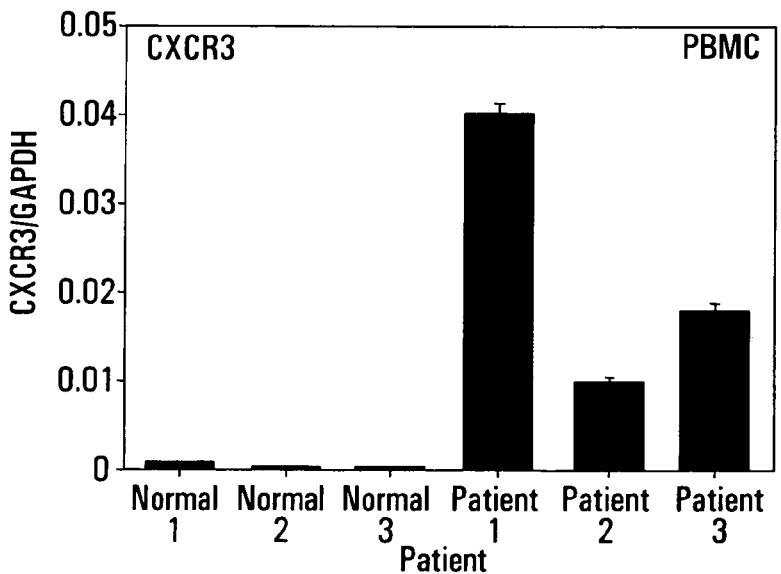

The persistence of elevated levels of CXCL10 polypeptide in patients with severe illness lead us to postulate that infected tissues may be the main source of CXCL10 polypeptide. Using real time PCR, we found that lung tissues from deceased individuals had elevated levels of CXCL10 polypeptide transcripts compared to tissue from normal lungs (FIG. 2A). We also determined whether SARS-infected lungs had increased levels of CXCR3 polypeptide. All lung samples with elevated levels of CXCL10 polypeptide also had elevated levels of CXCR3 polypeptide (FIG. 2B). Increased transcript levels of CXCL10 polypeptide and CXCR3 polypeptide could also be noted in PBMCs from confirmed SARS patients at 7 days (FIG. 3A,B). These data suggest that SARS CoV infection induces CXCL10 polypeptide expression that in turn recruits activated T cells into infected tissues.

Figure 3C:
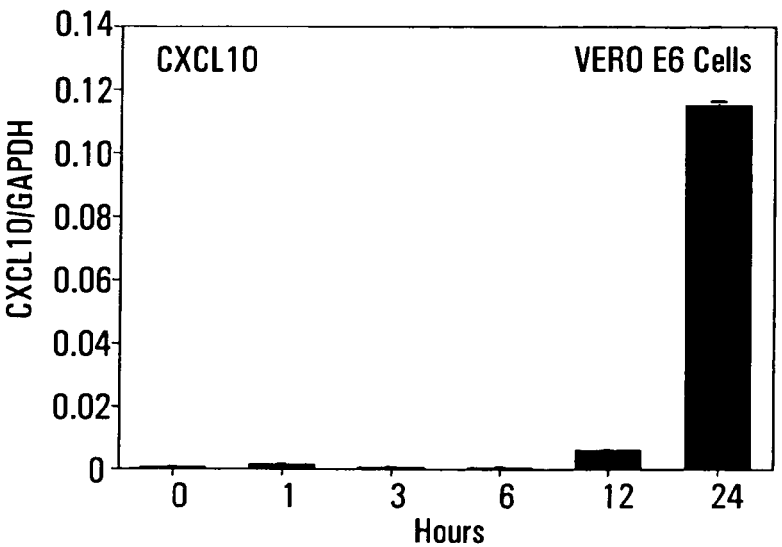
Figure 4A:
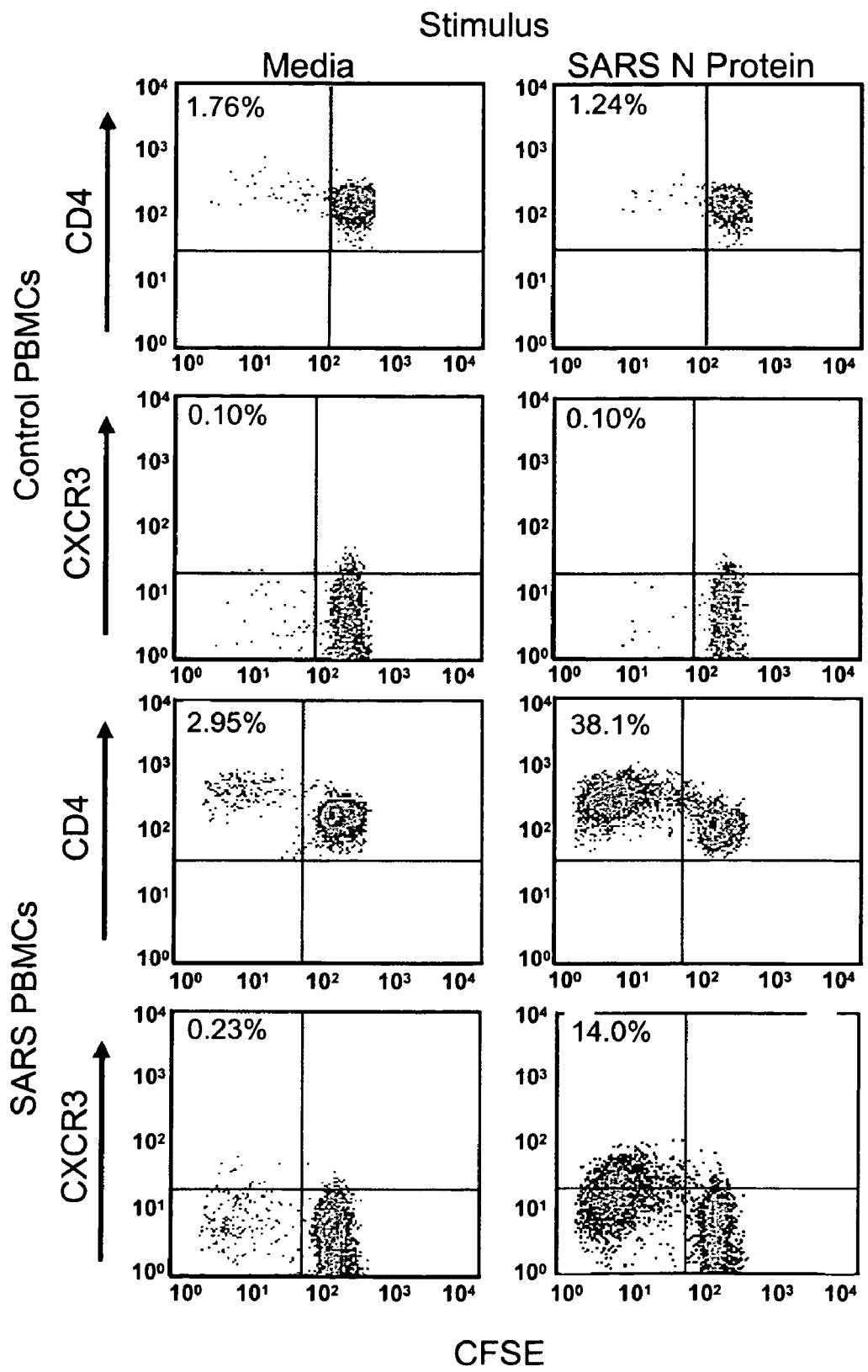
FIG. 4. High proliferative capacity of, and CXCR3 polypeptide expression by, SARS N protein-specific CD4$^+$ and CD8$^+$ T cells in convalescent SARS patients. $1\times10^6$ cryopreserved PBMCs from convalescent confirmed SARS patients were thawed, stained with CFSE and cultured in media alone or in the presence of recombinant SARS CoV N protein. After 6 d, we measured proliferating (CFSE$^{low}$) CD4$^+$ and CD8$^+$ T cells and CXCR3 polypeptide expression on proliferating CD4$^+$ and CD8$^+$ T cells from healthy controls (FIG. 4A) and convalescent SARS patients (FIG. 4B) by four FACS analysis. Results shown are representative of 5 randomly chosen convalescent SARS patients and 5 healthy controls. The numbers shown in the upper left quadrants are the percentage of CFSE$^{low}$ CD4$^+$ or CD8$^+$ T cells or those expressing CXCR3 polypeptide. 50 ng/ml SEA (Toxin Technology, Sarasota, Fla.) was used as a positive control. Average percentages following SEA stimulation were Control CD4$^+$ CFSE$^{low}$ 74% (range 67-88), SARS CD4$^+$ CFSE$^{low}$ 88% (range 83-92), Control CD4$^+$/CXCR3$^+$ CFSE$^{low}$ 20% (range 16-23), SARS CD4$^+$/CXCR3$^+$ CFSE$^{low}$ 22% (range 15-32), Control CD8$^+$ CFSE$^{low}$ 86% (range 81-92), SARS CD8$^+$ CFSE$^{low}$ 91% (range 85-96), Control CD8$^+$/CXCR3$^+$ CFSE$^{low}$ 63% (range 52-68), SARS CD4$^+$/CXCR3$^+$ CFSE$^{low}$ 55% (range 29-74).
Figure 4B:
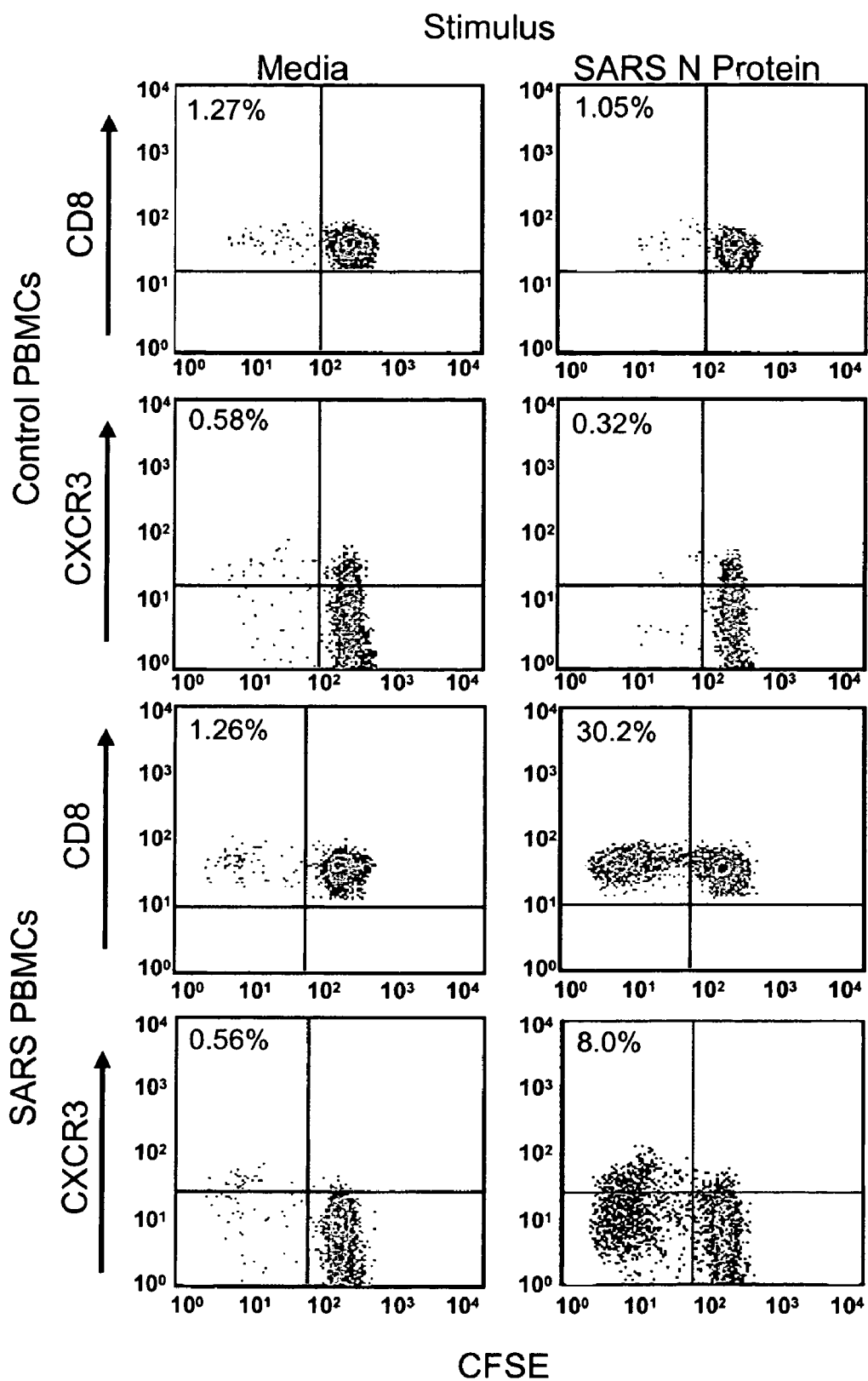

To test whether the SARS CoV itself may induce CXCL10 polypeptide expression, we conducted two experiments. Firstly, we found that SARS CoV infection of VERO E6 cells induced CXCL10 polypeptide expression in vitro within 12 hours (FIG. 3C). Secondly, we screened PBMCs of convalescent SARS patients for the presence of SARS antigen-specific, CXCR3 polypeptide-expressing T cell responses. We used a highly sensitive proliferation assay based on the labeling of T cells with the cell tracking dye CFSE (22). Cryopreserved PBMCs from convalescent confirmed SARS patients were thawed, stained with CFSE and cultured for 6 d in the presence of recombinant SARS CoV N protein. Using FACS, we quantitated proliferating (CFSE$^{low}$) CD4$^+$ or CD8$^+$ T cells from convalescent SARS patients and healthy controls and their expression of CXCR3 polypeptide. We found that a high proportion of CD4$^+$ and CD8$^+$ T cells from recovered SARS patients proliferated vigorously in response to SARS CoV N protein and that a high proportion of those expressed CXCR3 polypeptide (FIG. 4). This finding shows that proliferating SARS antigen-specific T cells express CXCR3 polypeptide and thus would have the capacity to infiltrate tissues expressing elevated levels of CXCL10 polypeptide.

Figure 5:
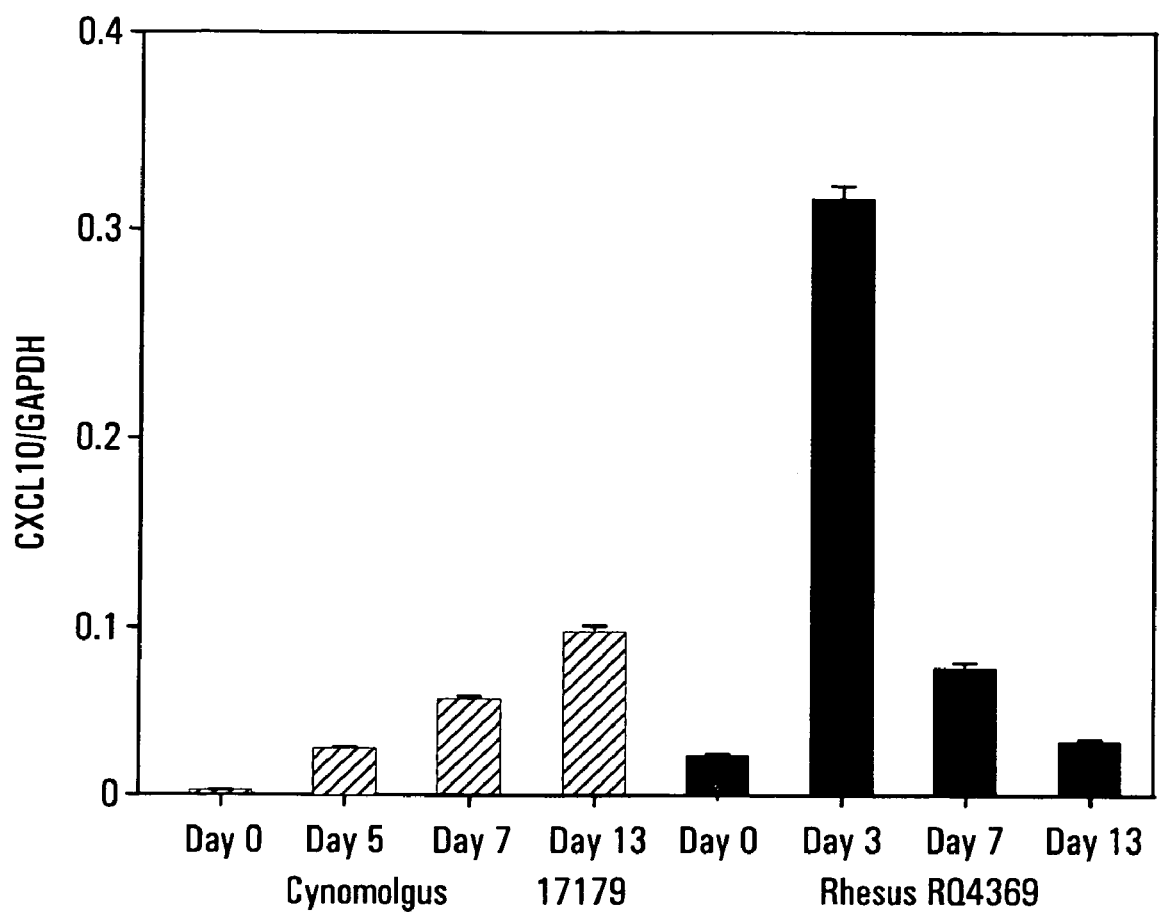
FIG. 5. PBMCs from macaques infected by SARS CoV express CXCL10 polypeptide within 3-5 days post-infection. Rhesus (n=4) and cynomolgus (n=4) macaques were inoculated with $1\times10^6$ p.f.u. SARS-COV (Tor2) intratracheally and monitored for 13 days. Blood samples were collected on the days shown and PBMC RNA was isolated. Real time PCR was performed using the human CXCL10 primers listed in the Methods and Materials and the relative expression of each gene is shown normalized to GAPDH. Results are shown for one representative cynomolgus and rhesus monkey. CXCL10 polypeptide/GAPDH ratios in PBMCs from day 0 monkeys and additional uninfected control monkeys (n=4) did not exceed 0.03.

Lastly, we confirmed that CXCL10 polypeptide expression could be induced in non-human primates following infection with SARS CoV. We examined longitudinal CXCL10 polypeptide expression by real time PCR in two macaque models of experimental SARS infection. We found that PBMCs isolated from cynomolgus and rhesus macaques inoculated with SARS CoV (Tor2) expressed increased CXCL10 polypeptide transcripts within 3-5 d post-infection (FIG. 5). During the 2 wk duration of this preliminary experiment, cynomolgus macaques (n=4) expressed CXCL10 polypeptide in increasing intensities (up to approx. 40-fold increase at day 13 relative to day 0), whereas CXCL10 polypeptide expression peaked in rhesus macaques (n=4) at day 3 (approx. 15-fold increase relative to day 0). CXCL10 polypeptide/GAPDH ratios in PBMCs from day 0 monkeys and additional uninfected control monkeys (n=4) were very small or negligible. Overall, these data indicate a role for the CXCL10:CXCR3 axis in SARS immunopathogenesis and in mediating host immune responses against SARS CoV infection during the course of disease.

Figure 6:
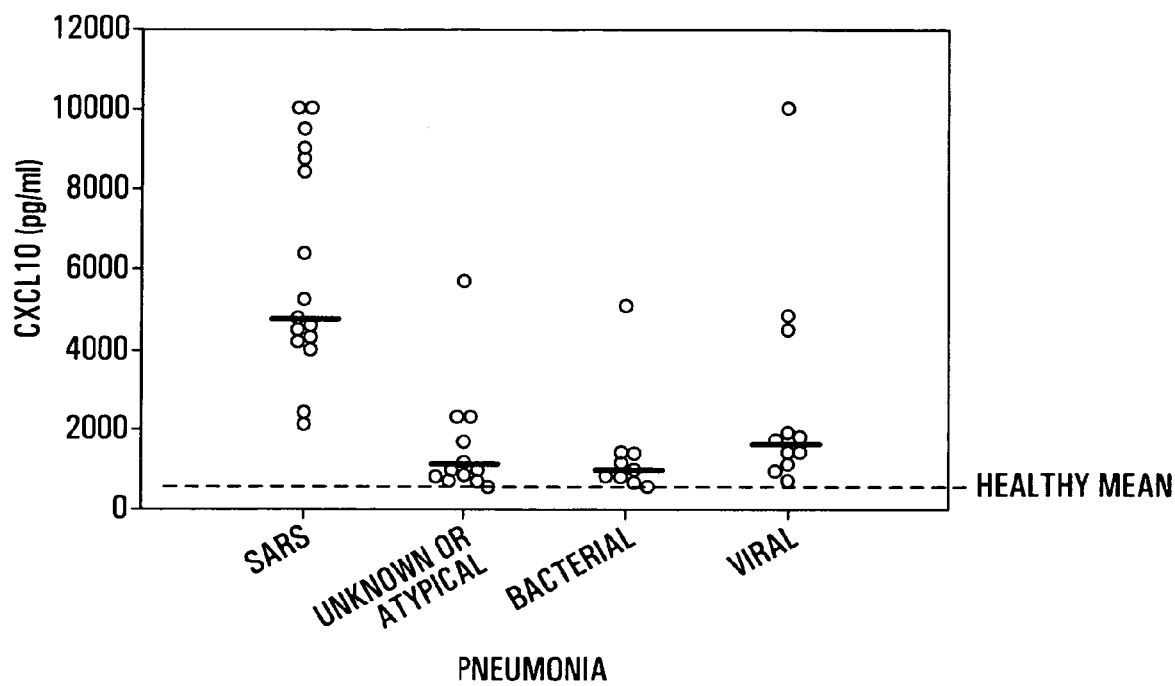
FIG. 6. High plasma concentrations of CXCL10 polypeptide in chest X-Ray positive SARS patients and some severe cases of community acquired pneumonia. CXCL10 polypeptide was measured in plasma from confirmed chest X-Ray positive SARS patients (n=16) within 7 d of onset of symptoms by CBA. CXCL10 polypeptide levels were also recorded in healthy controls (n=14, mean shown) and patients with chest X-Ray positive community acquired pneumonia (n=32). Causative agents are listed on the X axis.

Our CBA study of patients with community-acquired pneumonia whose presentations were initially confused with SARS indicated that some severe cases were associated with increases of CXCL10 polypeptide (FIG. 6).

Exemplary CXCL10 Polypeptide and CXCR3 Polypeptide and Amino Acid and Nucleotide Sequences:

(1) Human CXCL10 polypeptide amino acid sequence: GenBank accession No. NP_001556.1. (SEQ ID NO: 1).

```
  1 MNQTAILICC LIFLTLSGIQ GVPLSRTVRC TCISISNQPV NPRSLEKLEI IPASQFCPRV
 61 EIIATMKKKG EKRCLNPESK AIKNLLKAVS KEMSKRSP
```

(2) Human CXCL10 polypeptide mRNA sequence: GenBank accession No. NM_001565. (SEQ ID NO: 2).

```
    1 gagacattcc tcaattgctt agacatattc tgagcctaca gcagaggaac ctccagtctc
   61 agcaccatga atcaaactgc gattctgatt tgctgcctta tctttctgac tctaagtggc
  121 attcaaggag tacctctctc tagaaccgta cgctgtacct gcatcagcat tagtaatcaa
  181 cctgttaatc caaggtcttt agaaaaactt gaaattattc ctgcaagcca attttgtcca
  241 cgtgttgaga tcattgctac aatgaaaaag aagggtgaga gagatgtct gaatccagaa
  301 tcgaaggcca tcaagaattt actgaaagca gttagcaagg aaatgtctaa aagatctcct
  361 taaaaccaga ggggagcaaa atcgatgcag tgcttccaag gatggaccac acagaggctg
  421 cctctcccat cacttcccta catggagtat atgtcaagcc ataattgttc ttagtttgca
  481 gttacactaa aaggtgacca atgatggtca ccaaatcagc tgctactact cctgtaggaa
  541 ggttaatgtt catcatccta agctattcag taataactct accctggcac tataatgtaa
  601 gctctactga ggtgctatgt tcttagtgga tgttctgacc ctgcttcaaa tatttccctc
  661 acctttccca tcttccaagg gtactaagga atctttctgc tttggggttt atcagaattc
  721 tcagaatctc aaataactaa aaggtatgca atcaaatctg cttttaaag aatgctcttt
  781 acttcatgga cttccactgc catcctccca aggggcccaa attctttcag tggctaccta
  841 catacaattc caaacacata caggaaggta gaaatatctg aaaatgtatg tgtaagtatt
  901 cttatttaat gaaagactgt acaaagtata agtcttagat gtatatattt cctatattgt
  961 tttcagtgta catggaataa catgtaatta agtactatgt atcaatgagt aacaggaaaa
 1021 ttttaaaaat acagatagat atatgctctg catgttacat aagataaatg tgctgaatgg
 1081 ttttcaaata aaaatgaggt actctcctgg aaatattaag aaagactatc taaatgttga
 1141 aagatcaaaa ggttaataaa gtaattataa ct
```

(3) Murine CXCL10 polypeptide amino acid sequence: GenBank accession No. NP_067249.1. (SEQ ID NO: 3).

```
  1 MNPSAAVIFC LILLGLSGTQ GIPLARTVRC NCIHIDDGPV RMRAIGKLEI IPASLSCPRV
 61 EIIATMKKND EQRCLNPESK TIKNLMKAFS QKRSKRAP
```

(4) Murine CXCL10 polypeptide mRNA sequence: GenBank accession No. NM_021274.1. (SEQ ID NO: 4).

```
    1 catcccgagc caaccttccg gaagcctccc catcagcacc atgaacccaa gtgctgccgt
   61 cattttctgc ctcatcctgc tgggtctgag tgggactcaa gggatccctc tcgcaaggac
  121 ggtccgctgc aactgcatcc atatcgatga cgggccagtg agaatgaggg ccataggaa
```

-continued
```
 181 gcttgaaatc atccctgcga gcctatcctg cccacgtgtt gagatcattg ccacgatgaa
 241 aaagaatgat gagcagagat gtctgaatcc ggaatctaag accatcaaga atttaatgaa
 301 agcgtttagc caaaaaaggt ctaaaagggc tccttaactg gagtgaagcc acgcacacac
 361 cccggtgctg cgatggatgg acagcagaga gcctctctcc atcactcccc tttacccagt
 421 ggatggctag tcctaattgc ccttggtctt ctgaaaggtg accagccgtg gtcacatcag
 481 ctgctactcc tcctgcagga tgatggtcaa gccatggtcc tgagacaaaa gtaactgccg
 541 aagcaagaat tctttaaggg ctggtctgag tcctcgctca agtggctggg atggctgtcc
 601 tagctctgta ctgtaagcta tgtggaggtg cgacgccctt caccatgtgc catgcccagg
 661 ctgctcccca caccctcctt gtcctcccta gctcaggctc gtcagttcta agtttacctg
 721 agctcttttta tttcagatgt aagactacaa atttaagttt gtaagcacga acttaaccac
 781 catcttccca aggggttatc aagatactca gaggaacctg aaaatgtatg tgtaaatact
 841 atttaatgaa cgactgtaca aagtagaatt cctaatgtat tttttgtatg ctttgcattg
 901 tatatggaag aacttgtgtc atcaagtatg tatcaatggg tagttaaagt ttatttttaa
 961 aaccgtccaa tacctttttgt attatgtaac attcaaaaga caatgtactg tattgaaagt
1021 agtaagagac ccaaaatgta ataaagtaat aataactgac atg
```

(5) Human CXCR3 polypeptide mRNA sequence: GenBank accession No. NM_001504. (SEQ ID NO: 5).

```
   1 ccaaccacaa gcaccaaagc agaggggcag gcagcacacc acccagcagc cagagcacca
  61 gcccagccat ggtccttgag gtgagtgacc accaagtgct aaatgacgcc gaggttgccg
 121 ccctcctgga gaacttcagc tcttcctatg actatgagaa aaacgagagt gactcgtgct
 181 gtacctcccc gcccctgccca caggacttca gcctgaactt cgaccgggcc ttcctgccag
 241 ccctctacag cctcctcttt ctgctgggc tgctgggcaa cggcgcggtg gcagccgtgc
 301 tgctgagccg gcggacagcc ctgagcagca ccgacacctt cctgctccac ctagctgtag
 361 cagacacgct gctggtgctg acactgccgc tctgggcagt ggacgctgcc gtccagtggg
 421 tctttggctc tggcctctgc aaagtggcag gtgccctctt caacatcaac ttctacgcag
 481 gagcccctcct gctggcctgc atcagctttg accgctacct gaacatagtt catgccaccc
 541 agctctaccg ccgggggccc cggccgcgc tgaccctcac ctgcctggct gtctggggc
 601 tctgcctgct tttcgccctc ccagacttca tcttcctgtc ggcccaccac gacgagcgcc
 661 tcaacgccac ccactgccaa tacaacttcc cacaggtggg ccgcacggct ctgcgggtgc
 721 tgcagctggt ggctggcttt ctgctgcccc tgctggtcat ggcctactgc tatgcccaca
 781 tcctggccgt gctgctggtt ccaggggcc agcgcgcct gcgggccatg cggctggtgg
 841 tggtggtcgt ggtggccttt gccctctgct ggaccccta tcacctggtg gtgctggtgg
 901 acatcctcat ggaccttggg gctttggccc gcaactgtgg ccgagaaagc agggtagacg
 961 tggccaagtc ggtcacctca ggcctgggct acatgcactg ctgcctcaac ccgctgctct
1021 atgcctttgt aggggtcaag ttccgggagc ggatgtggat gctgctcttg cgcctgggct
1081 gccccaacca gagagggctc cagaggcagc atcgtcttc ccgccgggat tcatcctggt
1141 ctgagacctc agaggcctcc tactcgggct tgtgaggccg gaatccgggc tcccctttcg
1201 cccacagtct gacttccccg cattccaggc tcctccctcc ctctgccggc tctggctctc
1261 cccaatatcc tcgctcccgg gactcactgg cagccccagc accaccaggt ctcccgggaa
```

-continued

```
1321 gccaccctcc cagctctgag gactgcacca ttgctgctcc ttagctgcca agccccatcc
1381 tgccgcccga ggtggctgcc tggagcccca ctgcccttct catttggaaa ctaaaacttc
1441 atcttcccca agtgcgggga gtacaaggca tggcgtagag ggtgctgccc catgaagcca
1501 cagcccaggc ctccagctca gcagtgactg tggccatggt ccccaagacc tctatatttg
1561 ctcttttatt tttatgtcta aaatcctgct taaaactttt caataaacaa gatcgtcagg
1621 accaaaaaaa aaaaaaaaaa aaaaaaaaaa aaaaaaaaaa aaaaaaaaa
```

(6) Human CXCR3 polypeptide amino acid sequence:
GenBank accession No. NP_001495. (SEQ ID NO: 6).

```
  1 MVLEVSDHQV LNDAEVAALL ENFSSSYDYG ENESDSCCTS PPCPQDFSLN FDRAFLPALY
 61 SLLFLLGLLG NGAVAAVLLS RRTALSSTDT FLLHLAVADT LLVLTLPLWA VDAAVQWVFG
121 SGLCKVAGAL FNINFYAGAL LLACISFDRY LNIVHATQLY RRGPPARVTL TCLAVWGLCL
181 LFALPDFIFL SAHHDERLNA THCQYNFPQV GRTALRVLQL VAGFLLPLLV MAYCYAHILA
241 VLLVSRGQRR LRAMRLVVVV VVAFALCWTP YHLVVLVDIL MDLGALARNC GRESRVDVAK
301 SVTSGLGYMH CCLNPLLYAF VGVKFRERMW MLLLRLGCPN QRGLQRQPSS SRRDSSWSET
361 SEASYSGL
```

(7) Murine CXCR3 polypeptide amino acid sequence:
GenBank accession No. NP_034040.1. (SEQ ID NO: 7).

```
  1 MYLEVSERQV LDASDFAFLL ENSTSPYDYG ENESDFSDSP PCPQDFSLNF DRTFLPALYS
 61 LLFLLGLLGN GAVAAVLLSQ RTALSSTDTF LLHLAVADVL LVLTLPLWAV DAAVQWVFGP
121 GLCKVAGALF NINFYAGAFL LACISFDRYL SIVHATQIYR RDPRVRVALT CIVVWGLCLL
181 FALPDFIYLS ANYDQRLNAT HCQYNFPQVG RTALRVLQLV AGFLLPLLVM AYCYAHILAV
241 LLVSRGQRRF RAMRLVVVVV AAFAVCWTPY HLVVLVDILM DVGVLARNCG RESHVDVAKS
301 VTSGMGYMHC CLNPLLYAFV GVKFREQMWM LFTRLGRSDQ RGPQRQPSSS RRESSWSETT
361 EASYLGL
```

(8) Murine CXCR3 polypeptide mRNA sequence: GenBank accession No. NM_009910.1. (SEQ ID NO: 8).

```
  1 gcaagttccc aaccacaagt gccaaaggca gagaagcagg cagcacgaga cctgaccca
 61 gcagccacag ccggagcacc agccaagcca tgtaccttga ggttagtgaa cgtcaagtgc
121 tagatgcctc ggactttgcc tttcttctgg aaaacagcac ctctccctac gattatgggg
181 aaaacgagag cgacttctct gactccccgc cctgcccaca ggatttcagc ctgaactttg
241 acagaacctt cctgccagcc ctctacagcc tcctcttctt gctgggctg ctaggcaatg
301 gggcggtggc tgctgtgcta ctgagtcagc gcactgccct gagcagcacg gacaccttcc
361 tgctccacct ggctgtagcc gatgttctgc tggtgttaac tcttccattg tgggcagtgg
421 atgctgctgt ccagtgggtt ttcggccctg gcctctgcaa agtggcaggc gccttgttca
481 acatcaactt ctatgcaggg gccttcctgc tggcttgtat aagcttcgac agatatctga
541 gcatagtgca cgccacccag atctaccgca gggaccccg ggtacgtgta gccctcacct
```

-continued

```
601 gcatagttgt atggggtctc tgtctgctct ttgccctccc agatttcatc tacctatcag 661 ccaactacga tcagcgcctc aatgccaccc attgccagta caacttccca caggtgggtc 721 gcactgctct gcgtgtactg cagctagtgg ctggtttcct gctgcccctt ctggtcatgg 781 cctactgcta tgcccatatc ctagctgttc tgctggtctc cagaggccag aggcgttttc 841 gagctatgag gctagtggta gtggtggtgg cagccttttgc tgtctgctgg accccctatc 901 acctggtggt gctagtggat atcctcatgg atgtgggagt tttggcccgc aactgtggtc 961 gagaaagcca cgtggatgtg gccaagtcag tcacctcggg catggggtac atgcactgct 1021 gcctcaatcc gctgctctat gcctttgtgg gagtgaagtt cagagagcaa atgtggatgt 1081 tgttcacgcg cctgggccgc tctgaccaga gagggcccca gcggcagccg tcatcttcac 1141 ggagagaatc atcctggtct gagacaactg aggcctccta cctgggcttg taattctgga 1201 ctggaactgt agcctgcgca gcccaagtcc taacacactc caagtgcttg tcctcctggt 1261 agtttgggcta gctcgaactt acccgtaact ttgctgccag gatgcactga cagctcagca 1321 tatatccagc tctcctgaga atcaatctca gcaacaagga caacaccatt actgtgcctt 1381 agctgccatg ccctatcttg ctgttttaga actagctgcc tggagcccca ccgccctact 1441 aaattagcaa gtagaactca gccatccctg tgtgagaaga gggagaggca aatagcacag 1501 agggccaggc gttgtcagca ctgaatgtgc ccatctcagt atctcaatat ttgcccaatt 1561 ttatttctag aaacctcact taaactttca ataaacaagg taatgagg
```

REFERENCES

1. Tsang, K. W., P. L. Ho, G. C. Ooi, W. K. Yee, T. Wang, M. Chan-Yeung, W. K. Lam, W. H. Seto, L. Y. Yam, T. M. Cheung, P. C. Wong, B. Lam, M. S. Ip, J. Chan, K. Y. Yuen, and K. N. Lai. 2003. A cluster of cases of severe acute respiratory syndrome in Hong Kong. *N. Engl. J. Med.* 348:1977.
2. Lee, N., D. Hui, A. Wu, P. Chan, P. Cameron, G. M. Joynt, A. Ahuja, M. Y. Yung, C. B. Leung, K. F. To, S. F. Lui, C. C. Szeto, S. Chung, and J. J. Sung. 2003. A major outbreak of severe acute respiratory syndrome in Hong Kong. *N. Engl. J. Med.* 348:1986.
3. Poutanen, S. M., D. E. Low, B. Henry, S. Finkelstein, D. Rose, K. Green, R. Tellier, R. Draker, D. Adachi, M. Ayers, A. K. Chan, D. M. Skowronski, I. Salit, A. E. Simor, A. S. Slutsky, P. W. Doyle, M. Krajden, M. Petric, R. C. Brunham, and A. J. McGeer. 2003. Identification of severe acute respiratory syndrome in Canada. *N. Engl. J. Med.* 348:1995.
4. Centers for Disease Control and Prevention. 2003. Update: severe acute respiratory syndrome—worldwide and United States, 2003. *MMWR Morb. Mortal. Wkly. Rep.* 52:664.
5. Booth, C. M., L. M. Matukas, G. A. Tomlinson, A. R. Rachlis, D. B. Rose, H. A. Dwosh, S. L. Walmsley, T. Mazzulli, M. Avendano, P. Derkach, I. E. Ephtimios, I. Kitai, B. D. Mederski, S. B. Shadowitz, W. L. Gold, L. A. Hawryluck, E. Rea, J. S. Chenkin, D. W. Cescon, S. M. Poutanen, and A. S. Detsky. 2003. Clinical features and short-term outcomes of 144 patients with SARS in the greater Toronto area. *JAMA* 289:2801.
6. Ksiazek, T. G., D. Erdman, C. S. Goldsmith, S. R. Zaki, T. Peret, S. Emery, S. Tong, C. Urbani, J. A. Comer, W. Lim, P. E. Rollin, S. F. Dowell, A. E. Ling, C. D. Humphrey, W. J. Shieh, J. Guarner, C. D. Paddock, P. Rota, B. Fields, J. DeRisi, J. Y. Yang, N. Cox, J. M. Hughes, J. W. LeDuc, W. J. Bellini, and L. J. Anderson. 2003. A novel coronavirus associated with severe acute respiratory syndrome. *N. Engl. J. Med.* 348:1953.
7. Peiris, J. S., S. T. Lai, L. L. Poon, Y. Guan, L. Y. Yam, W. Lim, J. Nicholls, W. K. Yee, W. W. Yan, M. T. Cheung, V. C. Cheng, K. H. Chan, D. N. Tsang, R. W. Yung, T. K. Ng, and K. Y. Yuen. 2003. Coronavirus as a possible cause of severe acute respiratory syndrome. *Lancet* 361:1319.
8. Drosten, C., S. Gunther, W. Preiser, W. S. van der, H. R. Brodt, S. Becker, H. Rabenau, M. Panning, L. Kolesnikova, R. A. Fouchier, A. Berger, A. M. Burguiere, J. Cinatl, M. Eickmann, N. Escriou, K. Grywna, S. Kramme, J. C. Manuguerra, S. Muller, V. Rickerts, M. Sturmer, S. Vieth, H. D. Klenk, A. D. Osterhaus, H. Schmitz, and H. W. Doerr. 2003. Identification of a novel coronavirus in patients with severe acute respiratory syndrome. *N. Engl. J. Med.* 348:1967.
9. Cyranoski, D. 2004. Swift response greets return of SARS in China. *Nature* 427:89.
10. Zheng, B. J., K. H. Wong, J. Zhou, K. L. Wong, B. W. Young, L. W. Lu, and S. S. Lee. 2004. SARS-related virus predating SARS outbreak, Hong Kong. *Emerg. Infect. Dis.* 10:176.
11. Nicholls, J. M., L. L. Poon, K. C. Lee, W. F. Ng, S. T. Lai, C. Y. Leung, C. M. Chu, P. K. Hui, K. L. Mak, W. Lim, K. W. Yan, K. H. Chan, N. C. Tsang, Y. Guan, K. Y. Yuen, and J. S. Peiris. 2003. Lung pathology of fatal severe acute respiratory syndrome. *Lancet* 361:1773.
12. Mazzulli, T., G. A. Farcas, S. M. Poutanen, B. M. Willey, D. Low, J. Butany, S. L. Asa, and K. C. Kain. 2004. Severe acute respiratory syndrome-associated Coronavirus in lung tissue. *Emerg. Infect. Dis.* 10:20.
13. Hwang, D. M., Chamberlain, D. W., Poutanen, S. M., Low, D. E., Asa, S. A., and Butany, J. 2004. Pulmonary pathology of severe acute respiratory syndrome in Tor- 14. Ng, P. C., C. W. Lam, A. M. Li, C. K. Wong, F. W. Cheng, T. F. Leung, E. K. Hon, I. H. Chan, C. K. Li, K. S. Fung, and T. F. Fok. 2004. Inflammatory cytokine profile in children with severe acute respiratory syndrome. *Pediatrics* 113:e7.
15. Wong, C. K., Lam, C. W. K., Wu, A. K. L., Ip, W. K., Lee, N. L. S., Chan, I. H. S., Lit, L. C. W., Hui, D. S. C., Chan, M. H. M., Chung, S. S. C., and Sung, J. J. Y. 2004. Plasma inflammatory cytokines and chemokines in severe acute respiratory syndrome. *Clin. Exp. Immunol.* 136:95.
16. Lee, C. H., Chen, R. F., Liu, J. W., Yeh, W. T., Chang, J. C., Liu, P. M., Eng, H. L., Lin, M. C., and Yang, K. D. 2004. Altered p38 mitogen-activated protein kinase expression in different leukocytes with increment of immunosuppressive mediators in patients with severe acute respiratory syndrome. *J. Immunol.* 172:7841
17. Dufour, J. H., Dziejman, M., Liu, M. T., Leung, J. H., Lane, T. E., and Luster, A. D. 2002. IFN-γ-inducible protein 10 (IP-10; CXCL10)-deficient mice reveal a role for IP-10 in effector T cell generation and trafficking. *J. Immunol.* 168:3195.
18. Liu, M. T., Keirstead, H. S., and Lane, T. E. 2001. Neutralization of the chemokine CXCL10 reduces inflammatory cell invasion and demyelination and improves neurological function in a viral model of multiple sclerosis. *J. Immunol.* 167:4091.
19. Trifilo, M. J., Montalto-Morrison, C., Stiles, L. N., Hurst, K. R., Hardison, J. L., Manning, J. E., Masters, P. S., and Lane, T. E. 2004. CXC chemokine ligand 10 controls viral infection in the central nervous system: evidence for a role in innate immune response through recruitment and activation of natural killer cells. *J. Virol.* 78:585
20. Liu, M. T., B. P. Chen, P. Oertel, M. J. Buchmeier, T. A. Hamilton, D. A. Armstrong, and T. E. Lane. 2001. The CXC chemokines IP-10 and Mig are essential in host defense following infection with a neurotropic coronavirus. *Adv. Exp. Med. Biol.* 494:323.
21. Knowles, S. R., Phillips, E. J., Dresser, L., and Matukas, L. 2003. Common adverse events associated with the use of ribavirin for severe acute respiratory syndrome in Canada. *Clin. Infect. Dis.* 37:1139.
22. Younes, S. A., B. Yassine-Diab, A. R. Dumont, M. R. Boulassel, Z. Grossman, J. P. Routy, and R. P. Sekaly. 2003. HIV-1 viremia prevents the establishment of interleukin 2-producing HIV-specific memory CD4+ T cells endowed with proliferative capacity. *J. Exp. Med.* 198:1909.
23. Sorensen, T. L., Sellebjerg, F., Jensen, C. V., Strieter, R. M., and Ransohoff, R. M. 2001. Chemokines CXCL10 and CCL2: differential involvement in intrathecal inflammation in multiple sclerosis. *Eur. J. Neurol.* 8:665.
24. Sauty, A., M. Dziejman, R. A. Taha, A. S. Iarossi, K. Neote, E. A. Garcia-Zepeda, Q. Hamid, and A. D. Luster. 1999. The T cell-specific CXC chemokines IP-10, Mig, and I-TAC are expressed by activated human bronchial epithelial cells. *J. Immunol.* 162:3549.
25. Ranieri, V. M., P. M. Suter, C. Tortorella, R. De Tullio, J. M. Dayer, A. Brienza, F. Bruno, and A. S. Slutsky. 1999. Effect of mechanical ventilation on inflammatory mediators in patients with acute respiratory distress syndrome: a randomized controlled trial. *JAMA* 282:54.
26. Enserink, M. 2003. SARS researchers report new animal models. *Science* 302:213
27. Kuiken, T., Fouchier, R. A., Scutten, M., Rimmelzwaan, G. F., van Amerongen, G., van Riel, D., Laman, J. D., de Jong, T., van Doornum, G., Lim, W., Ling, A. E., Chan, P. K., Tam, J. S., Zambon, M. C., Gopal, R., Drosten, C., van der Werf, S., Escriou, N., Manuguerra, J. C., Stohr, K., Peiris, J. S., and Osterhaus, A. D. 2003. Newly discovered coronavirus as the primary cause of severe acute respiratory syndrome. *Lancet* 362:263.
28. Luster, A. D. 1998. Chemokines—chemotactic cytokines that mediate inflammation. *N. Engl. J. Med.* 338:436.
29. Rossi, D., and Zlotnik, A. 2000. The biology of chemokines and their receptors. *Annu. Rev. Immunol.* 18:217.
30. Melchjorsen, J., Sorensen, L. N., and Paludan, S. R. 2003, Expression and function of chemokines during viral infections: from molecular mechanisms to in vivo function. *J. Leukoc. Biol.* 74:331.
31. Sorensen, T. L., C. Trebst, P. Kivisakk, K. L. Klaege, A. Majmudar, R. Ravid, H. Lassmann, D. B. Olsen, R. M. Strieter, R. M. Ransohoff, and F. Sellebjerg. 2002. Multiple sclerosis: a study of CXCL10 and CXCR3 co-localization in the inflamed central nervous system. *J. Neuroimmunol.* 127:59.
32. Nicoletti, F., I. Conget, M. Di Mauro, R. Di Marco, M. C. Mazzarino, K. Bendtzen, A. Messina, and R. Gomis. 2002. Serum concentrations of the interferon-gamma-inducible chemokine IP-10/CXCL10 are augmented in both newly diagnosed Type I diabetes mellitus patients and subjects at risk of developing the disease. *Diabetologia* 45:1107.
33. Patel, D. D., J. P. Zachariah, and L. P. Whichard. 2001. CXCR3 and CCR5 ligands in rheumatoid arthritis synovium. *Clin. Immunol.* 98:39.
34. Christen, U., McGavern, D. B., Luster, A. D., von Herrath, M. G., and Oldstone, M. B. 2003. Among CXCR3 chemokines, IFN-γ-inducible protein of 10 kDa (CXC chemokine ligand (CXCL) 10) but not monokine induced by IFN-γ (CXCL9) imprints a pattern for the subsequent development of autoimmune disease. *J. Immunol.* 171:683

The invention claimed is:

1. A method for monitoring the course of treatment of a patient suffering from respiratory illness associated with human Severe Acute Respiratory Syndrome coronavirus (SARS CoV) infection, wherein said patient is undergoing treatment of respiratory illness associated with human Severe Acute Respiratory Syndrome coronavirus (SARS CoV) infection, the method comprising determining the level of CXCL10 polypeptide in a test biological sample obtained from said patient; wherein a decrease in said level relative to a corresponding level of CXCL10 polypeptide determined in the same type of biological sample obtained from said patient at least 48 hours prior to obtaining said test biological sample is indicative that said patient is responsive to said treatment, wherein said method is used for monitoring the course of treatment of the patient.

2. The method of claim 1, wherein said biological sample is a blood sample.

3. The method of claim 1, wherein said step of determining comprises a cytometric bead array (CBA) assay.

* * * * *